US008421625B2

(12) United States Patent
Cowburn

(10) Patent No.: US 8,421,625 B2
(45) Date of Patent: Apr. 16, 2013

(54) SYSTEM AND METHOD FOR ARTICLE AUTHENTICATION USING THUMBNAIL SIGNATURES

(75) Inventor: Russell Paul Cowburn, London (GB)

(73) Assignee: Ingenia Holdings Limited, Road Town (VG)

( * ) Notice: Subject to any disclaimer, the term of this patent is extended or adjusted under 35 U.S.C. 154(b) by 215 days.

(21) Appl. No.: 12/951,884

(22) Filed: Nov. 22, 2010

(65) Prior Publication Data

US 2011/0109429 A1    May 12, 2011

Related U.S. Application Data

(62) Division of application No. 10/592,554, filed as application No. PCT/GB2005/000922 on Mar. 9, 2005, now Pat. No. 7,853, 792.

(60) Provisional application No. 60/610,075, filed on Sep. 15, 2004, provisional application No. 60/601,463, filed on Aug. 13, 2004.

(30) Foreign Application Priority Data

Mar. 12, 2004 (GB) .................................. 0405641.2
Sep. 15, 2004 (GB) .................................. 0420524.1

(51) Int. Cl.
*G08B 13/14* (2006.01)
*G06F 7/04* (2006.01)
*G06K 9/00* (2006.01)

(52) U.S. Cl.
USPC ......... 340/568.7; 340/5.8; 340/5.83; 382/100

(58) Field of Classification Search ............... 340/686.1, 340/686.5, 686.6, 686.7, 686.8, 571, 572.1, 340/572.4, 568.1, 568.5, 568.6, 568.7, 568.8, 340/5.8, 5.81, 5.82, 5.83; 235/382, 440, 235/454, 487, 488; 705/57, 76; 713/176; 382/100, 181, 280
See application file for complete search history.

(56) References Cited

U.S. PATENT DOCUMENTS 3,781,109 A    12/1973    Mayer, Jr. et al.
3,877,019 A    4/1975    Auerbach et al.
(Continued)

FOREIGN PATENT DOCUMENTS

CA    2292594    12/1998
CN    1588847    3/2005
(Continued)

OTHER PUBLICATIONS

Written Opinion for PCT/GB2007/000015 mailed May 4, 2007.
(Continued)

*Primary Examiner* — Van T. Trieu
(74) *Attorney, Agent, or Firm* — McDonnell Boehnen Hulbert & Berghoff LLP

(57) ABSTRACT

A method and apparatus for determining a digital signature from an article. A coherent light source directs a beam to illuminate the article and a detector arrangement collects data points from light scattered from many different parts of the article to collect a large number of independent data points, typically 500 or more. By collecting a large number of independent signal contributions specific to many different parts of the article, a digital signature can be computed that is unique to the area of the article that has been scanned. This measurement can be repeated whenever required to test authenticity of the article. Using this method, it has been discovered that it is essentially pointless to go to the effort and expense of making specially prepared tokens, since unique characteristics are measurable a in a straightforward manner from a wide variety of every day articles.

30 Claims, 11 Drawing Sheets

U.S. PATENT DOCUMENTS

| | | | |
|---|---|---|---|
| 4,179,212 A | 12/1979 | Lahr | |
| 4,218,674 A | 8/1980 | Brosow et al. | |
| 4,423,415 A | 12/1983 | Goldman | |
| 4,525,748 A | 6/1985 | Carbone | |
| 4,537,504 A | 8/1985 | Baltes et al. | |
| 4,544,266 A | 10/1985 | Antes | |
| 4,568,936 A | 2/1986 | Goldman | |
| 4,599,509 A | 7/1986 | Silverman et al. | |
| 4,738,901 A | 4/1988 | Finkel et al. | |
| 4,748,316 A | 5/1988 | Dickson | |
| 4,785,290 A | 11/1988 | Goldman et al. | |
| 4,791,669 A | 12/1988 | Kage | |
| 4,797,921 A | 1/1989 | Shiraishi | |
| 4,817,176 A | 3/1989 | Marshall et al. | |
| 4,820,912 A | 4/1989 | Samyn | |
| 4,920,385 A | 4/1990 | Clarke et al. | |
| 4,929,821 A | 5/1990 | Kocznar et al. | |
| 5,003,596 A | 3/1991 | Wood | |
| 5,054,066 A | 10/1991 | Riek et al. | |
| 5,058,164 A | 10/1991 | Elmer et al. | |
| 5,059,776 A | 10/1991 | Antes | |
| 5,060,065 A | 10/1991 | Wasserman | |
| 5,081,675 A | 1/1992 | Kittirusunetorn | |
| 5,103,479 A | 4/1992 | Takaragi et al. | |
| 5,120,126 A | 6/1992 | Wertz et al. | |
| 5,133,601 A | 7/1992 | Cohen et al. | |
| 5,142,578 A | 8/1992 | Matyas et al. | |
| 5,194,918 A | 3/1993 | Kino et al. | |
| 5,243,405 A | 9/1993 | Tichenor et al. | |
| 5,258,605 A | 11/1993 | Metlitsky et al. | |
| 5,295,196 A | 3/1994 | Raterman et al. | |
| 5,306,899 A | 4/1994 | Marom et al. | |
| 5,307,423 A | 4/1994 | Gupta et al. | |
| 5,325,167 A | 6/1994 | Melen | |
| 5,384,717 A | 1/1995 | Ebenstein | |
| 5,451,759 A | 9/1995 | Hoshino et al. | |
| 5,453,840 A | 9/1995 | Parker et al. | |
| 5,475,694 A | 12/1995 | Ivanov et al. | |
| 5,485,312 A | 1/1996 | Horner et al. | |
| 5,488,661 A | 1/1996 | Matsui | |
| 5,510,199 A | 4/1996 | Martin | |
| 5,521,984 A | 5/1996 | Deneberg et al. | |
| 5,539,840 A | 7/1996 | Krtolica et al. | |
| 5,546,462 A | 8/1996 | Indeck et al. | |
| 5,637,854 A | 6/1997 | Thomas | |
| 5,647,010 A | 7/1997 | Okubo et al. | |
| 5,673,338 A | 9/1997 | Denenberg et al. | |
| 5,687,002 A | 11/1997 | Itoh | |
| 5,760,386 A | 6/1998 | Ward | |
| 5,767,988 A | 6/1998 | Dobbs et al. | |
| 5,781,708 A | 7/1998 | Austin et al. | |
| 5,784,463 A | 7/1998 | Chen et al. | |
| 5,790,025 A | 8/1998 | Amer et al. | |
| 5,886,798 A | 3/1999 | Staub et al. | |
| 5,903,340 A | 5/1999 | Lawandy et al. | |
| 5,903,721 A | 5/1999 | Sixtus | |
| 5,912,974 A | 6/1999 | Holloway et al. | |
| 6,029,150 A | 2/2000 | Kravitz | |
| 6,141,119 A | 10/2000 | Tseng et al. | |
| 6,182,892 B1 | 2/2001 | Angelo et al. | |
| 6,193,156 B1 | 2/2001 | Han et al. | |
| 6,223,166 B1 | 4/2001 | Kay | |
| 6,265,907 B1 | 7/2001 | Sukegawa | |
| 6,280,797 B1 | 8/2001 | Kuczynski et al. | |
| 6,314,409 B2 | 11/2001 | Schneck et al. | |
| 6,328,209 B1 * | 12/2001 | O'Boyle | 235/380 |
| 6,332,663 B1 | 12/2001 | Puzio | |
| 6,360,001 B1 | 3/2002 | Berger et al. | |
| 6,373,573 B1 | 4/2002 | Jung | |
| 6,389,151 B1 | 5/2002 | Carr et al. | |
| 6,390,368 B1 | 5/2002 | Edwards | |
| 6,466,329 B1 | 10/2002 | Mukai | |
| 6,473,165 B1 | 10/2002 | Coombs et al. | |
| 6,529,269 B1 * | 3/2003 | Sugata | 356/71 |
| 6,560,355 B2 | 5/2003 | Graves et al. | |
| 6,563,129 B1 | 5/2003 | Knobel | |
| 6,584,214 B1 | 6/2003 | Pappu et al. | |
| 6,603,874 B1 | 8/2003 | Stern et al. | |
| 6,621,916 B1 | 9/2003 | Smith et al. | |
| 6,741,360 B2 | 5/2004 | D'Agraives et al. | |
| 6,760,472 B1 | 7/2004 | Takeda et al. | |
| 6,779,720 B2 | 8/2004 | Lewis | |
| 6,798,900 B1 * | 9/2004 | Sugata | 382/137 |
| 6,850,147 B2 | 2/2005 | Prokoski et al. | |
| 6,882,738 B2 | 4/2005 | Davis et al. | |
| 6,902,111 B2 * | 6/2005 | Han et al. | 235/454 |
| 6,928,552 B1 | 8/2005 | Mischenko et al. | |
| 6,950,094 B2 | 9/2005 | Gordon et al. | |
| 6,955,141 B2 | 10/2005 | Santanam et al. | |
| 6,961,449 B2 | 11/2005 | Mil'shtein | |
| 6,970,573 B2 | 11/2005 | Carr et al. | |
| 6,977,791 B2 | 12/2005 | Zhu et al. | |
| 7,002,675 B2 | 2/2006 | Macgibbon | |
| 7,031,555 B2 | 4/2006 | Troyanker | |
| 7,071,481 B2 | 7/2006 | Nekrasov et al. | |
| 7,076,084 B2 | 7/2006 | Davis et al. | |
| 7,077,332 B2 | 7/2006 | Verschuur et al. | |
| 7,080,041 B2 | 7/2006 | Nagel | |
| 7,082,216 B2 | 7/2006 | Jones et al. | |
| 7,089,420 B1 * | 8/2006 | Durst et al. | 713/176 |
| 7,104,449 B2 | 9/2006 | Han et al. | |
| 7,110,573 B2 | 9/2006 | Monk et al. | |
| 7,111,321 B1 | 9/2006 | Watts, Jr. et al. | |
| 7,119,662 B1 | 10/2006 | Horigucchi et al. | |
| 7,143,949 B1 | 12/2006 | Hannigan | |
| 7,152,047 B1 | 12/2006 | Nagel | |
| 7,162,035 B1 * | 1/2007 | Durst et al. | 380/54 |
| 7,164,810 B2 * | 1/2007 | Schnee et al. | 382/313 |
| 7,170,391 B2 | 1/2007 | Lane et al. | |
| 7,184,133 B2 | 2/2007 | Coombs et al. | |
| 7,200,868 B2 | 4/2007 | Mattox et al. | |
| 7,221,445 B2 | 5/2007 | Earthman et al. | |
| 7,222,361 B2 | 5/2007 | Kemper | |
| 7,251,347 B2 | 7/2007 | Smith | |
| 7,268,923 B2 | 9/2007 | Schroath et al. | |
| 7,277,183 B2 | 10/2007 | Deck | |
| 7,318,048 B1 | 1/2008 | King | |
| 7,333,629 B2 | 2/2008 | Patton et al. | |
| 7,336,842 B2 | 2/2008 | Kondo | |
| 7,346,184 B1 | 3/2008 | Carr et al. | |
| 7,353,994 B2 | 4/2008 | Farrall et al. | |
| 7,363,505 B2 | 4/2008 | Black | |
| 7,389,420 B2 * | 6/2008 | Tian | 713/176 |
| 7,389,530 B2 | 6/2008 | Raghunath et al. | |
| 7,391,889 B2 | 6/2008 | Kim et al. | |
| 7,394,573 B1 * | 7/2008 | Goldberg et al. | 358/3.28 |
| 7,497,379 B2 | 3/2009 | Chen | |
| 7,506,365 B2 | 3/2009 | Hirano et al. | |
| 7,567,349 B2 | 7/2009 | Tearney et al. | |
| 7,577,844 B2 | 8/2009 | Kirovski | |
| 7,599,927 B2 | 10/2009 | Lebrat | |
| 7,599,963 B2 | 10/2009 | Fernandez | |
| 7,602,904 B2 | 10/2009 | Juels et al. | |
| 7,605,940 B2 | 10/2009 | Silverbrook et al. | |
| 7,647,279 B2 | 1/2010 | Bourrieres et al. | |
| 7,684,069 B2 | 3/2010 | Kashiwaki | |
| 7,716,297 B1 | 5/2010 | Wittel et al. | |
| 7,853,792 B2 | 12/2010 | Cowburn | |
| 7,920,714 B2 | 4/2011 | O'Neil | |
| 8,009,800 B2 | 8/2011 | Doyle et al. | |
| 8,078,875 B2 | 12/2011 | Cowburn et al. | |
| 2002/0041787 A1 | 4/2002 | Thomas | |
| 2002/0091555 A1 | 7/2002 | Leppink | |
| 2002/0105654 A1 | 8/2002 | Goltsos | |
| 2002/0111837 A1 | 8/2002 | Aupperle | |
| 2002/0116329 A1 | 8/2002 | Serbetcioglu et al. | |
| 2003/0002067 A1 | 1/2003 | Miyano | |
| 2003/0012374 A1 | 1/2003 | Wu et al. | |
| 2003/0018587 A1 | 1/2003 | Althoff et al. | |
| 2003/0028494 A1 | 2/2003 | King et al. | |
| 2003/0035539 A1 | 2/2003 | Thaxton | |
| 2003/0118191 A1 | 6/2003 | Wang et al. | |
| 2003/0178487 A1 | 9/2003 | Rogers | |
| 2004/0016810 A1 | 1/2004 | Hori et al. | |
| 2004/0031849 A1 | 2/2004 | Hori et al. | |
| 2004/0059952 A1 | 3/2004 | Newport et al. | |
| 2004/0101158 A1 | 5/2004 | Butler et al. | |

| | | | |
|---|---|---|---|
| 2004/0155913 A1 | 8/2004 | Kosugi et al. | |
| 2004/0199765 A1 | 10/2004 | Kohane et al. | |
| 2005/0044385 A1 | 2/2005 | Holdsworth | |
| 2005/0060171 A1 | 3/2005 | Molnar | |
| 2005/0101841 A9 | 5/2005 | Kaylor et al. | |
| 2005/0108057 A1 | 5/2005 | Cohen et al. | |
| 2005/0135260 A1 | 6/2005 | Todd | |
| 2005/0178841 A1 | 8/2005 | Jones et al. | |
| 2006/0022059 A1 | 2/2006 | Juds | |
| 2006/0104103 A1 | 5/2006 | Colineau et al. | |
| 2006/0163504 A1 | 7/2006 | Fujimoto et al. | |
| 2006/0166381 A1 | 7/2006 | Lange | |
| 2006/0256959 A1 | 11/2006 | Hymes | |
| 2006/0294583 A1 | 12/2006 | Cowburn et al. | |
| 2007/0025619 A1 | 2/2007 | Cowburn et al. | |
| 2007/0027819 A1 | 2/2007 | Cowburn | |
| 2007/0028093 A1 | 2/2007 | Cowburn et al. | |
| 2007/0028107 A1 | 2/2007 | Cowburn et al. | |
| 2007/0028108 A1 | 2/2007 | Cowburn et al. | |
| 2007/0036470 A1 | 2/2007 | Piersol et al. | |
| 2007/0053005 A1 | 3/2007 | Cowburn | |
| 2007/0058037 A1 | 3/2007 | Bergeron et al. | |
| 2007/0113076 A1 | 5/2007 | Cowburn et al. | |
| 2007/0115497 A1 | 5/2007 | Cowburn | |
| 2007/0136612 A1 | 6/2007 | Asano et al. | |
| 2007/0153078 A1 | 7/2007 | Cowburn | |
| 2007/0162961 A1 | 7/2007 | Tarrance et al. | |
| 2007/0164729 A1 | 7/2007 | Cowburn et al. | |
| 2007/0165208 A1 | 7/2007 | Cowburn et al. | |
| 2007/0188793 A1 | 8/2007 | Wakai | |
| 2007/0192850 A1 | 8/2007 | Cowburn | |
| 2007/0199047 A1 | 8/2007 | Gibart et al. | |
| 2007/0271456 A1 | 11/2007 | Ward et al. | |
| 2008/0022243 A1 | 1/2008 | Cowburn | |
| 2008/0016358 A1 | 1/2008 | Filreis et al. | |
| 2008/0044096 A1 | 2/2008 | Cowburn et al. | |
| 2008/0051033 A1 | 2/2008 | Hymes | |
| 2008/0260199 A1 | 10/2008 | Cowburn et al. | |
| 2008/0294900 A1 | 11/2008 | Cowburn | |
| 2009/0016535 A1 | 1/2009 | Cowburn | |
| 2009/0083372 A1 | 3/2009 | Teppler | |
| 2009/0254991 A1 | 10/2009 | Boulanger et al. | |
| 2009/0283583 A1 | 11/2009 | Cowburn | |
| 2009/0290906 A1 | 11/2009 | Cowburn | |
| 2009/0303000 A1 | 12/2009 | Cowburn | |
| 2009/0307112 A1 | 12/2009 | Cowburn | |
| 2010/0007930 A1 | 1/2010 | Cowburn | |
| 2010/0008590 A1 | 1/2010 | Cowburn | |
| 2010/0141380 A1 | 6/2010 | Pishva | |
| 2010/0158377 A1 | 6/2010 | Cowburn et al. | |
| 2010/0161529 A1 | 6/2010 | Cowburn et al. | |
| 2010/0277446 A1 | 11/2010 | van Veenendaal et al. | |

FOREIGN PATENT DOCUMENTS

| | | |
|---|---|---|
| DE | 19632269 | 2/1997 |
| DE | 19612819 | 10/1997 |
| DE | 10155780 | 5/2003 |
| DE | 10234431 | 2/2004 |
| EP | 0 234 105 | 9/1987 |
| EP | 0 278 058 | 8/1988 |
| EP | 0 334 201 | 9/1989 |
| EP | 0378198 | 7/1990 |
| EP | 0 472 192 | 2/1992 |
| EP | 0 480 620 | 4/1992 |
| EP | 0 570 162 | 11/1993 |
| EP | 0 590 826 | 4/1994 |
| EP | 0 691 632 | 1/1996 |
| EP | 1 087 348 | 3/2001 |
| EP | 1202225 | 5/2002 |
| EP | 1217589 | 6/2002 |
| EP | 1 273 461 | 1/2003 |
| EP | 1 286 315 | 2/2003 |
| EP | 1 388 797 | 2/2004 |
| EP | 1 418 542 | 5/2004 |
| EP | 1 434 161 | 6/2004 |
| EP | 1484719 | 12/2004 |
| EP | 1 507 227 | 2/2005 |
| EP | 1 577 812 | 9/2005 |
| EP | 1587030 | 10/2005 |
| EP | 1 616 711 | 12/2005 |
| EP | 1 990 779 | 11/2008 |
| GB | 1319928 | 3/1972 |
| GB | 1458726 | 12/1976 |
| GB | 2097979 | 11/1982 |
| GB | 2221870 | 2/1990 |
| GB | 2228821 | 9/1990 |
| GB | 2411954 | 9/1995 |
| GB | 2304077 | 3/1997 |
| GB | 2346110 | 1/2000 |
| GB | 2346111 | 1/2000 |
| GB | 2417074 | 2/2006 |
| GB | 2417592 | 3/2006 |
| GB | 2417707 | 3/2006 |
| GB | 2426100 | 11/2006 |
| GB | 2428846 | 2/2007 |
| GB | 2428948 | 2/2007 |
| GB | 2429092 | 2/2007 |
| GB | 2429097 | 2/2007 |
| GB | 2431759 | 5/2007 |
| GB | 2433632 | 6/2007 |
| GB | 2434642 | 8/2007 |
| JP | H02-10482 | 1/1990 |
| JP | 2183879 | 7/1990 |
| JP | H03-192523 | 8/1991 |
| JP | 04265847 | 9/1992 |
| JP | H05-504220 | 7/1993 |
| JP | H06-301840 | 10/1994 |
| JP | 07210721 | 8/1995 |
| JP | H08-003548 | 1/1996 |
| JP | H08-180189 | 7/1996 |
| JP | 09218910 | 8/1997 |
| JP | 63255793 | 10/1998 |
| JP | H11-224319 | 8/1999 |
| JP | 11339049 | 12/1999 |
| JP | 2000011230 | 1/2000 |
| JP | 2000149087 | 5/2000 |
| JP | 2000293105 | 10/2000 |
| JP | 2001521658 | 11/2001 |
| JP | 2002-092682 | 3/2002 |
| JP | 2004102562 | 4/2002 |
| JP | 2003509745 | 3/2003 |
| JP | 2003-141595 | 5/2003 |
| JP | 2003143388 | 5/2003 |
| JP | 2003150585 | 5/2003 |
| JP | 2003228709 | 8/2003 |
| JP | 2003534536 | 11/2003 |
| JP | 2004077954 | 3/2004 |
| JP | 2004171109 | 6/2004 |
| JP | 2005038389 | 2/2005 |
| JP | 2005217805 | 8/2005 |
| JP | 2005352854 | 12/2005 |
| KR | 200523050 | 8/2003 |
| NL | 8002604 | 12/1981 |
| NL | 9401796 C | 10/1994 |
| RU | 2043201 | 9/1995 |
| RU | 2065819 | 8/1996 |
| TW | 437229 | 5/2001 |
| TW | 570444 | 1/2004 |
| WO | 89/00742 | 1/1989 |
| WO | 91/11703 | 8/1991 |
| WO | 91/11778 | 8/1991 |
| WO | 91/19614 | 12/1991 |
| WO | 93/22745 | 11/1993 |
| WO | 95/24691 | 9/1995 |
| WO | 95/34018 | 12/1995 |
| WO | 96/36934 | 11/1996 |
| WO | 97/24699 | 7/1997 |
| WO | 99/13391 | 3/1999 |
| WO | 00/45344 | 8/2000 |
| WO | 00/46980 | 8/2000 |
| WO | 00/65541 | 11/2000 |
| WO | 01/18754 | 3/2001 |
| WO | 01/25024 | 4/2001 |
| WO | 01/43086 | 6/2001 |
| WO | 01/54077 | 7/2001 |
| WO | 01/86574 | 11/2001 |
| WO | 01/86589 | 11/2001 |
| WO | 01/91007 | 11/2001 |

| | | |
|---|---|---|
| WO | 02/50790 | 6/2002 |
| WO | 03/087991 | 10/2003 |
| WO | 2004/025548 | 3/2004 |
| WO | 2004/025549 | 3/2004 |
| WO | 2004/057525 | 7/2004 |
| WO | 2004/070667 | 8/2004 |
| WO | 2004/097826 | 11/2004 |
| WO | 2004/109479 | 12/2004 |
| WO | 2005/004039 | 1/2005 |
| WO | 2005/004797 | 1/2005 |
| WO | 2005/027032 | 3/2005 |
| WO | 2005/029447 | 3/2005 |
| WO | 2005/048256 | 5/2005 |
| WO | 2005/078651 | 8/2005 |
| WO | 2005/080088 | 9/2005 |
| WO | 2005/086158 | 9/2005 |
| WO | 2005/088517 | 9/2005 |
| WO | 2005/088533 | 9/2005 |
| WO | 2005/122100 | 12/2005 |
| WO | 2006/016112 | 2/2006 |
| WO | 2006/016114 | 2/2006 |
| WO | 2006/021083 | 3/2006 |
| WO | 2006/132584 | 12/2006 |
| WO | 2007/012815 | 2/2007 |
| WO | 2007/012821 | 2/2007 |
| WO | 2007/028799 | 3/2007 |
| WO | 2007/072044 | 6/2007 |
| WO | 2007/080375 | 7/2007 |
| WO | 2007/111548 | 10/2007 |
| WO | 2007/144598 | 12/2007 |
| WO | 2009/141576 | 11/2009 |
| WO | 2010/004281 | 1/2010 |
| WO | 2010/004282 | 1/2010 |

OTHER PUBLICATIONS

Anderson, R., "Security Engineering: A Guide to Building Dependable Distributed Systems," Wiley 2001, pp. 251-252.
Anonymous, "Discs and paper get biometric identifiers," IEEE Review, vol. 50, No. 12, p. 23, (Dec. 2004).
Buchanan, James, "Fingerprinting Documents and Packaging," Nature, 436:475 (Jul. 28, 2005).
Chen, Yuqun et al., "Certifying Authenticity via Fiber-Infused Paper," ACM SIG ecom Exchanges, 5(3):29-37 (2005).
Cowburn, Russell, "Nanotechnology-Security and Brand Protection Applications 01," Smart Brand and Product Protection Conference 2005, Apr. 8, 2005 to Apr. 9, 2005, pp. 1-4, London, UK.
Derrode S et al., "Robust and Efficient Fourier-Mellin Transform Approximations for Gray-Level Image Reconstruction and Complete Invariant Description," Computer Vision and Image Understanding, Academic Press, San Diego, CA, 83(1):57-78 (Jul. 2001).
El-Khamy S. E. et al., "The FBG stream cipher," Proceedings of the 24th Radio National Science Conference (NRSC 2007) IEEE Cairo, Egypt, pp. 1-8 (Mar. 2007).
International Search Report and Written Opinion for PCT/GB2008/002020 dated Jun. 16, 2009.
International Search Report for Great Britain Patent Application No. GB0711461.4 dated Sep. 21, 2007.
Haist et al., "Optical detection of random features for high security applications," Optics Communications, 147:173-179 (1998).
Hao F. et al., "Combining crypto with biometrics effectively," IEEE Transactions on Computers IEEE USA, 55 (9):1081-1088 (Sep. 2006).
Huss G. et al., "Spatial filtering efficiency of single-mode optical fibers for stellar interferometry applications: phenomenological and numerical study," Optics Communications, North-Holland Publishing Co., Amsterdam, NL, 244:209-217 (Sep. 23, 2004).
International Search Report issued by UK Intellectual Property Office for GB0607867.9 dated Aug. 22, 2006.
International Search Report for PCT/GB2005/0009222 dated Jun. 10, 2005.
International Search Report for PCT/GB2007/002173 dated Sep. 19, 2007.
International Search Report for PCT/GB2009/001702 dated Oct. 23, 2009.
Search Report for GB0720673.3 dated Mar. 28, 2008.
Kirovski, Darko, "Toward an Automated Verification of Certificates of Authenticity," pp. 160-169 (2004).
Kravolec, "Plastic Tag Makes Foolproof ID," Technology Research News, Oct. 2, 2002.
Kvasnik et al., "Image recognition using surface scattered light in a coherent optical processor," Image Processing and its Applications, University of Manchester Institute of Science and Technology UK, pp. 361-364 (1992).
Pappu et al., "Physical one-way functions," Science, American Association for the Advancement of Science, vol. 297, No. 5589, pp. 2026-2030 (2002).
Ravikanth, Pappu Srinivasa. "Physical One-Way Functions," Thesis at the Massachusetts Institute of Technology, pp. 1-154, Mar. 2001.
Schneier B., "Applied Cryptography. Protocols, Algorithms, and Source Code in C, Passage," Applied Cryptography, 2nd Ed., John Wiley & Sons, Inc., New York, p. 197 (1996).
Simmons, G.J., A survey of information authentication, In <i> Contemporary Cryptology, The Science of Information Integrity </i>, pp. 379-419 IEEE Press (1992).
Smith et al., "Microstructure Based Indicia," Laboratories Escher Group, pp. 1-5 (1999).
UK Search Report for GB0812772.2 dated Nov. 6, 2008.
UK Search Report for GB0812773 dated Mar. 2009.
UK Search Report for GB0812773 dated Nov. 2008.
Van Renesse R.L., "Optical inspection techniques for security instrumentation," Proceedings of SPIE—The International Society for Optical Engineering, Vo. 2659, pp. 159-167 (Mar. 1996).
Wilkes, Sally, "Fighting Fraud: Document Biometrics," Materials World, vol. 12, No. 12, pp. 29-30 (Dec. 2004).
Zhang D et al., "Shape-based image retrieval using generic Fourier descriptor," Signal Processing. Image Communication, Ellsevier Science Publishers, Amsterdam, NL 17(10):825-848 (Nov. 2002).
d'Agraives et al., "Surface Topography, A Remarkable Method for the Identification of Seals of Structures in General," Commission of the European Communities Joint Research Centre—Ispra Establishment I-21020 Ispra (Va), Italy, pp. 403-409 (1981).
Zwick/Roell—Zwick Materials Testing—the new direction in extension measurement—optiXtens, pp. 1-11 (2003).
Smalley, Eric, "Plastic tag makes foolproof ID," Technology Research News, Technology Research News LLC, Oct. 2, 2002 (2 pages).

* cited by examiner

SYSTEM AND METHOD FOR ARTICLE AUTHENTICATION USING THUMBNAIL SIGNATURES

This application is a divisional of U.S. application Ser. No. 10/592,554, filed Sep. 12, 2006, now U.S. Pat. No. 7,853,792, which is a National Stage of International Application No. PCT/GB2005/000922, filed Mar. 9, 2005, which claims priority to Great Britain Patent Application No. 0405641.2, filed Mar. 12, 2004, U.S. Provisional Application No. 60/601,463, filed Aug. 13, 2004, U.S. Provisional Application No. 60/610,075, filed Sep. 15, 2004, and Great Britain Patent Application No. 0420524.1, filed Sep. 15, 2004.

BACKGROUND OF THE INVENTION

The invention relates to security methods, more especially verification of authenticity of an article such as an personal identification (ID) card, vendable product, important document or other item.

Many traditional authentication security systems rely on a process which is difficult for anybody other than the manufacturer to perform, where the difficulty may be imposed by expense of capital equipment, complexity of technical know-how or preferably both. Examples are the provision of a watermark in bank notes and a hologram on credit cards or passports. Unfortunately, criminals are becoming more sophisticated and can reproduce virtually anything that original manufacturers can do.

Because of this, there is a known approach to authentication security systems which relies on creating security tokens using some process governed by laws of nature which results in each token being unique, and more importantly having a unique characteristic that is measurable and can thus be used as a basis for subsequent verification. According to this approach tokens are manufactured and measured in a set way to obtain a unique characteristic. The characteristic can then be stored in a computer database, or otherwise retained. Tokens of this type can be embedded in the carrier article, e.g. a banknote, passport, ID card, important document. Subsequently, the carrier article can be measured again and the measured characteristic compared with the characteristics stored in the database to establish if there is a match.

Within this general approach it has been proposed to use different physical effects. One effect that has been considered is to measure a magnetic response characteristic from depositions of magnetic materials, where each sample has a unique magnetic response as a result of naturally occurring defects in the magnetic material which form in an irreproducible manner [1]. Another effect that has been considered in a number of prior art documents is to use laser speckle from intrinsic properties of an article to provide a unique characteristic.

GB 2 221 870 A [2] discloses a method in which a security device, such as an ID card, effectively has a token embossed on it. The form of the token is a structured surface derived from a master. The speckle pattern from the light scattering structure is unique to the master and therefore can be measured to prove authenticity of the token on the security device. The token on the security device is measured in a reader which has a laser for generating a coherent beam of a size roughly equal to the token (2 mm diameter) and a detector, such as a charged coupled device (CCD) detector, for measuring the speckle pattern created by the interaction of the laser beam with the token. The resulting data is recorded. For verification, a security device can be placed in the reader and its recorded speckle pattern signal compared against a similar recorded signal from a reference device created from the same master.

U.S. Pat. No. 6,584,214 [3] describes an alternative to using speckle patterns in reflection from a specially prepared surface structure, in which speckle patterns are instead used in transmission from a specially prepared transparent token. The preferred implementation of this technique is to prepare epoxy tokens of dimension approximately 1 cm×1 cm in which glass spheres are embedded. The tokens are prepared by mixing the glass spheres in a colloidal suspension in a liquid polymer, which is then cured to fix the positions of the glass spheres. The unique ensemble of glass spheres is then probed using a coherent laser beam in transmission with a CCD detector positioned to measure the speckle pattern. In a modification of this approach, a known identifier is encoded on a reflective surface which is then stuck to one side of the token. The probing light passes through the token, is reflected by the known identifier and passes through the token again. The glass spheres thus modify the speckle pattern so that a unique hashed key is generated from the known identifier.

Kralovec [4] briefly reports that in the 1980's workers at Sandia National Laboratories in the US experimented with special banknote paper which was impregnated with chopped-up optical fibres. A speckle pattern could be measured from the optical fibres and a digitally signed version of this printed as a barcode on the side of the note. However, Kralovec reports that this idea could not be made to work properly, because the optical fibres were too fragile and the speckle pattern changed rapidly when the banknote was circulated owing to wear. This meant that the speckle pattern measured from the optical fibres in a used banknote no longer matched the bar-code, so the banknote could no longer be authenticated from the speckle pattern in the intended manner.

Anderson [5] on page 251 of his 2001 text book also briefly refers to what appears to be a similar scheme to that described by Kravolec [4] which is used for monitoring arms control agreements. Anderson observes that many materials have surfaces that are unique or that can be made so by eroding them with a small explosive charge. This is said to make it easy to identify capital equipment such as heavy artillery, where identifying each gun barrel is enough to prevent cheating by either party to an arms control agreement. Anderson reports that the surface pattern of the gun barrel is measured using laser speckle techniques, and either recorded in a log or attached to the device as a machine-readable digital signature.

Instead of using laser speckle, there is a more-straightforward group of proposed schemes that simply image an article at high resolution and use this high resolution image as the unique characteristic, which can then be re-imaged subsequently for verification of authenticity. This may be regarded as an adaptation of the conventional approach used for fingerprint libraries held by police forces.

U.S. Pat. No. 5,521,984 [6] proposes using an optical microscope to take an image of a small area of a valuable article, such as a painting, sculpture, stamp, gem or specific document.

Anderson [5] on page 252 of his 2001 text book reports that postal systems were considering schemes of this kind based on direct imaging of envelopes with a microscope. It is reported that an image of the paper fibres of an envelope is made, a pattern extracted, and recorded in the postal franking mark, which is digitally signed.

U.S. Pat. No. 5,325,167 [7] proposes imaging the grain structure of toner particles on a part of a valuable document following a similar scheme.

Through this previous work, there are various desirable features that are apparent for an ideal verification scheme.

The reported magnetic or speckle based techniques appear to be capable of providing high security levels, but require special materials to be prepared [1, 2, 3] for practical implementation to ensure long-term stability of the probed structure [4]. In many cases, integration of a token into the article to be secured is non-trivial. Particularly, integration of a resin token or a magnetic chip in paper or cardboard is not easy and involves significant cost. For integration with paper or cardboard, any token should ideally be printable. Additionally, there is also an inherent security risk of an attachable token-based approach in that the token is potentially detachable and attachable to a different article.

The reported direct imaging techniques [5, 6, 7] have the advantage that they obtain their digital signature directly from the article, obviating the need for special tokens. However, their intrinsic security is low. For example they are vulnerable to fraudulent access to the stored image data which may allow fabrication of an article that could be verified incorrectly as being authentic, or to forging by simply using a high resolution printer to print an image of what would be seen under a microscope when viewing the relevant part of the genuine article. The security level of direct imaging techniques also scales with the volume of the image data, forcing use of expensive high resolution imaging equipment for higher security levels. This may be acceptable in some applications, such as postal sorting or banknote verification, but in many applications will be unacceptable.

SUMMARY OF THE INVENTION

The present invention resulted from the inventor's work on applying authentication techniques using tokens made of magnetic materials, where the uniqueness is provided by unreproducible defects in the magnetic material that affect the token's magnetic response [1]. As part of this work, magnetic materials were fabricated in barcode format, i.e. as a number of parallel strips. As well as reading the unique magnetic response of the strips by sweeping a magnetic field with a magnetic reader, an optical scanner was built to read the barcodes by scanning a laser beam over the barcode and using contrast from the varying reflectivity of the barcode strips and the article on which they were formed. This information was complementary to the magnetic characteristic, since the barcode was being used to encode a digital signature of the unique magnetic response in a type of well known self authentication scheme, for example as also described above for banknotes [4].

To the surprise of the inventor, it was discovered when using this optical scanner that the paper background material on which the magnetic chips were supported gave a unique optical response to the scanner. On further investigation, it was established that many other unprepared surfaces, such as surfaces of various types of cardboard and plastic, show the same effect. Moreover, it has been established by the inventor that the unique characteristic arises at least in part from speckle, but also includes non-speckle contributions.

It has thus been discovered that it is possible to gain all the advantages of speckle based techniques without having to use a specially prepared token or specially prepare an article in any other way. In particular, many types of paper and cardboard have been found to give unique characteristic scattering signals from a coherent light beam, so that unique digital signatures can be obtained from almost any paper document or cardboard packaging item.

The above-described prior art speckle readers used for security devices appear to be based on illuminating the whole of a token with a collimated, i.e. unfocused, laser beam and imaging a significant solid angle portion of the resultant speckle pattern with a CCD [2, 3], thereby obtaining a speckle pattern image of the token made up of a large array of data points.

The reader used by the inventor does not operate in this manner. It uses four single channel detectors (four simple phototransistors) which are angularly spaced apart to collect only four signal components from the scattered laser beam. The laser beam is focused to a spot covering only a very small part of the surface. Signal is collected from different localised areas on the surface by the four single channel detectors as the spot is scanned over the surface. The characteristic response from the article is thus made up of independent measurements from a large number (typically hundreds or thousands) of different localised areas on the article surface. Although four phototransistors are used, analysis using only data from a single one of the phototransistors shows that a unique characteristic response can be derived from this single channel alone! However, higher security levels are obtained if further ones of the four channels are included in the response.

According to one aspect of the invention there is thus provided an apparatus for determining a signature from an article arranged in a reading volume, comprising: a source for generating a coherent beam; a detector arrangement for collecting a set of data points from signals obtained when the coherent beam scatters from the reading volume, wherein different ones of the data points relate to scatter from different parts of the reading volume; and a data acquisition and processing module for determining a signature of the article from the set of data points.

In some embodiments, it is ensured that different ones of the data points relate to scatter from different parts of the reading volume by providing a drive for causing the coherent beam to move over the reading volume and the coherent beam is dimensioned to have a cross-section substantially smaller than a projection of the reading volume in a plane normal to the coherent beam so that the coherent beam samples different parts of the reading volume under action of the drive. The drive may be provided by an electric motor that moves the beam over an article that is held fixed. The drive motor could be a servo motor, free running motor, stepper motor or any suitable motor type. Alternatively, the drive could be manual in a low cost reader. For example, the operator could scan the beam over the reading volume by moving a carriage on which the article is mounted across a static beam. The coherent beam cross-section will usually be at least one order of magnitude (preferably at least two) smaller than the projection of the reading volume so that a significant number of independent data points can be collected. A focusing arrangement may be provided for bringing the coherent beam into focus in the reading volume. The focusing arrangement may be configured to bring the coherent beam to an elongate focus, in which case the drive is preferably configured to move the coherent beam over the reading volume in a direction transverse to the major axis of the elongate focus. An elongate focus can conveniently be provided with a cylindrical lens, or equivalent mirror arrangement.

In other embodiments, it can be ensured that different ones of the data points relate to scatter from different parts of the reading volume, in that the detector arrangement includes a plurality of detector channels arranged and configured to sense scatter from respective different parts of the reading volume. This can be achieved with directional detectors, local collection of signal with optical fibres or other measures.

With directional detectors or other localised collection of signal, the coherent beam does not need to be focused. Indeed, the coherent beam could be static and illuminate the whole sampling volume. Directional detectors could be implemented by focusing lenses fused to, or otherwise fixed in relation to, the detector elements. Optical fibres may be used in conjunction with microlenses.

The reader may further comprise a housing for accommodating at least a part of the detector arrangement and having a reading aperture against which an article is placeable so that it is positioned in the reading volume. For field use, it is envisaged that the reader will be a self-contained unit based around a housing with a reading aperture. An article to be authenticated, e.g. by a customs officer or trading standards officer, can then be placed in a set position over the reading aperture. The reading aperture will typically be covered by a transparent window to avoid ingress of dirt into the optical components.

Other forms of the reader may be more suitable for production line use. For example, the reader may further comprise an article conveyor for moving an article past the coherent beam, or more likely a succession of similar articles. In a production environment, the coherent beam may be static and the articles moved through it. For example, packaging boxes of perfume may pass by on a conveyor at a set height and intersect a horizontal laser beam.

A physical location aid for positioning an article of a given form in a fixed position in relation to the reading volume will be useful in many cases. It will be appreciated that only a small portion of an article, such as an item of packaging or a piece of paper, or a passport, will usually be used to obtain the signature. Consequently it is important when re-reading an article for authentication that the same part of the article is measured as was done originally. To assist this physical location aids can be useful.

Various detector arrangements could be used.

It is possible to make a workable reader when the detector arrangement consists of only a single detector channel. Other embodiments use a detector arrangement that comprises a group of detector elements angularly distributed and operable to collect a group of data points for each different part of the reading volume, preferably a small group of a few detector elements. Security enhancement is provided when the signature incorporates a contribution from a comparison between data points of the same group. This comparison may conveniently involve a cross-correlation.

Although a working reader can be made with only one detector channel, there are preferably at least 2 channels. This allows cross-correlations between the detector signals to be made, which is useful for the signal processing associated with determining the signature. It is envisaged that between 2 and 10 detector channels will be suitable for most applications with 2 to 4 currently being considered as the optimum balance between apparatus simplicity and security.

The detector elements are advantageously arranged to lie in a plane intersecting the reading volume with each member of the pair being angularly distributed in the plane in relation to the coherent beam axis, preferably with one or more detector elements either side of the beam axis. However, non-planar detector arrangements are also acceptable.

The use of cross-correlations of the signals obtained from the different detectors has been found to give valuable data for increasing the security levels and also for allowing the signatures to be more reliably reproducible over time. The utility of the cross-correlations is somewhat surprising from a scientific point of view, since speckle patterns are inherently uncorrelated (with the exception of signals from opposed points in the pattern). In other words, for a speckle pattern there will by definition be zero cross-correlation between the signals from the different detectors so long as they are not arranged at equal magnitude angles offset from the excitation location in a common plane intersecting the excitation location. The value of using cross-correlation contributions therefore indicates that an important part of the scatter signal is not speckle. The non-speckle contribution could be viewed as being the result of direct scatter, or a diffuse scattering contribution, from a complex surface, such as paper fibre twists. At present the relative importance of the speckle and non-speckle scatter signal contribution is not clear. However, it is clear from the experiments performed to date that the detectors are not measuring a pure speckle pattern, but a composite signal with speckle and non-speckle components.

Incorporating a cross-correlation component in the signature is also of benefit for improving security. This is because, even if it is possible using high resolution printing to make an article that reproduces the contrast variations over the surface of the genuine article, this would not be able to match the cross-correlation coefficients obtained by scanning the genuine article.

In the main embodiment, the detector channels are made up of discrete detector components in the form of simple phototransistors. Other simple discrete components could be used such as PIN diodes or photodiodes. Integrated detector components, such as a detector array could also be used, although this would add to the cost and complexity of the device.

From initial experiments which modify the illumination angle of the laser beam on the article to be scanned, it also seems to be important in practice that the laser beam is incident approximately normal to the surface being scanned in order to obtain a characteristic that can be repeatedly measured from the same surface with little change, even when the article is degraded between measurements. At least some prior art readers use oblique incidence [2]. Once appreciated, this effect seems obvious, but it is clearly not immediately apparent as evidenced by the design of some prior art speckle readers including that of Ezra et al [2] and indeed the first prototype reader built by the inventor. The inventor's first prototype reader with oblique incidence functioned reasonably well in laboratory conditions, but was quite sensitive to degradation of the paper used as the article. For example, rubbing the paper with fingers was sufficient to cause significant differences to appear upon re-measurement. The second prototype reader used normal incidence and has been found to be robust against degradation of paper by routine handling, and also more severe events such as: passing through various types of printer including a laser printer, passing through a photocopier machine, writing on, printing on, deliberate scorching in an oven, and crushing and reflattening.

It can therefore be advantageous to mount the source so as to direct the coherent beam onto the reading volume so that it will strike an article with near normal incidence. By near normal incidence means±5, 10 or 20 degrees. Alternatively, the beam can be directed to have oblique incidence on the articles. This will usually have a negative influence in the case that the beam is scanned over the article.

It is also noted that in the readers described in the detailed description, the detector arrangement is arranged in reflection to detect radiation back scattered from the reading volume. However, if the article is transparent, the detectors could be arranged in transmission.

In one group of embodiments, the data acquisition and processing module is operable to further analyse the data points to identify a signal component that follows a predetermined encoding protocol and to generate a reference signature therefrom. The characteristic of the predetermined encoding protocol is envisaged to be based on contrast, i.e. scatter signal strength, in most embodiments. In particular, a conventional bar code protocol may be used in which the bar code is printed or otherwise applied to the article in the form of stripes in the case of a 1D barcode or more complex patterns for a 2D bar code. In this case, the data acquisition and processing module can be operable to perform a comparison to establish whether the reference signature matches the signature obtained by reading an article that has been placed in the reading volume. Consequently, an article such as a piece of paper, can be marked to bear a digitally signed version of its own characteristic, such as a barcode. The reference signature should be obtained from the article's characteristic with a one-way function, i.e. using an asymmetric encryption algorithm that requires a private key. This acts as a barrier to an unauthorised third party with a reader, who wants to read fake articles and print on them a label that represents the reader's scan according to the encryption scheme. Typically the bar code label or other mark would represent a cryptogram decipherable by a public key, and the private key would be reserved for the authorised labellor party.

A database of previously recorded signatures may be provided, wherein the data acquisition and processing module is operable to access the database and perform a comparison to establish whether the database contains a match to the signature of an article that has been placed in the reading volume. The database may be part of a mass storage device that forms part of the reader apparatus, or may be at a remote location and accessed by the reader through a telecommunications link. The telecommunications link may take any conventional form, including wireless and fixed links, and may be available over the internet. The data acquisition and processing module may be operable, at least in some operational modes, to allow the signature to be added to the database if no match is found. This facility will usually only be allowed to authorised persons for obvious reasons.

When using a database, in addition to storing the signature it may also be useful to associate that signature in the database with other information about the article such as a scanned copy of the document, a photograph of a passport holder, details on the place and time of manufacture of the product, or details on the intended sales destination of vendable goods (e.g. to track grey importation).

Reader apparatuses as described above may be used in order to populate a database with signatures by reading a succession of articles, e.g. in a production line, and/or in order subsequently to verify authenticity of an article, e.g. in field use.

The invention allows identification of articles made of a variety of different kinds of materials, such as paper, cardboard and plastic.

The invention allows it to be ascertained whether an article has been tampered with. This is possible if adhesively bonded transparent films, such as adhesive tape, cover the scanned area used to create the signature. If the tape must be removed to tamper with the article, e.g. to open a packaging box, the adhesive bonding can be selected so that it will inevitably modify the underlying surface. Consequently, even if similar tape is used to reseal the box, this will be detectable.

The invention provides a method of identifying an article made of paper or cardboard, comprising: exposing the paper or cardboard to coherent radiation; collecting a set of data points that measure scatter of the coherent radiation from intrinsic structure of the paper or cardboard; and determining a signature of the article from the set of data points.

By intrinsic structure we mean structure that the article inherently will have by virtue of its manufacture, thereby distinguishing over structure specifically provided for security purposes, such as structure given by tokens or artificial fibres incorporated in the article.

By paper or cardboard we mean any article made from wood pulp process. The paper or cardboard may be treated with coatings or impregnations or covered with transparent material, such as Cellophane™. If long-term stability of the surface is a particular concern, the paper may be treated with an acrylic spray-on transparent coating, for example.

Data points can thus be collected as a function of position of illumination by the coherent beam. This can be achieved either by scanning a localised coherent beam over the article, or by using directional detectors to collect scattered light from different parts of the article, or by a combination of both.

The invention is considered to be particularly useful for paper or cardboard articles from the following list of examples:

1. valuable documents such as share certificates, bills of lading, passports, intergovernmental treaties, statutes, driving licenses, vehicle roadworthiness certificates, any certificate of authenticity
2. any document for tracing or tracking purposes, e.g. envelopes for mail systems, banknotes for law enforcement tracking
3. packaging of vendable products
4. brand labels on designer goods, such as fashion items
5. packaging of cosmetics, pharmaceuticals, or other products
6. CD's and DVD's either on the disk itself, e.g. near the centre, or on the case.

The invention also provides a method of identifying an article made of plastic, comprising: exposing the plastic to coherent radiation; collecting a set of data points that measure scatter of the coherent radiation from intrinsic structure of the plastic; and determining a signature of the article from the set of data points.

If the plastic is opaque to the coherent radiation, the scatter will be from intrinsic surface structure of the plastic, whereas if the plastic is transparent, the scatter may arise from any part of the article impinged upon by the coherent radiation.

The invention is considered to be particularly useful for plastic articles from the following list of examples:

1. plastic packaging, for example of pharmaceuticals
2. ID cards, including bank cards, staff ID cards, store cards—including the signed strip on an ID card, especially a bank or store card Particularly useful applications may be scanning over the signed strip of an ID card, i.e. after signing, so that digital signature used for authenticity is specific to the signed card and is formed from a combination of the person's signature and the surface structure of the underlying strip.

In the case of an ID article bearing a photograph of a person (which may be a plastic ID card or a pass from other material such as a paper passport) it may be useful for the reader to scan over the photograph part of the ID card (separate from scanning the cover or a blank page) as a test that no tampering has occurred. This is because, if a coating or adhesive film is used to attach a photograph to the ID article, it must be removed by a forger in order to fix a fake photograph into the ID article. This type of forgery would be identified by a reader implementing the present invention, since the new photograph would have a different surface structure.

It is expected that any other material type will be identifiable by the invention provided that it has suitable surface structure. Material types that have very smooth surfaces at a microscopic level may be unsuitable as may be opaque materials that have a very deep and/or unstable surface (e.g. fleece material).

The invention also allows identification of articles of a variety of different types, including packaging, documents, and clothing.

The invention provides a method of identifying a product by its packaging, comprising: exposing the packaging of the product to coherent radiation; collecting a set of data points that measure scatter of the coherent radiation from intrinsic structure of the packaging; and determining a signature of the product from the set of data points.

The relevant part of the packaging exposed to the coherent radiation may be made of paper, cardboard, plastic (e.g. Cellophane™ shrink wrap), metal or other material with suitable intrinsic surface or internal structure. The article may be contained in the packaging, and optionally the packaging may be seabed in a tamper-proof manner. Alternatively, the packaging may be an appendage to the article, such as a tag secured with a connector that cannot be released without being visibly damaged. This may be especially useful for pharmaceutical products, cosmetic goods and perfume, and spare parts for aircraft or land or water vehicles, for example.

The invention provides a method of identifying a document, comprising: exposing the document to coherent radiation; collecting a set of data points that measure scatter of the coherent radiation from intrinsic structure of the document; and determining a signature of the document from the set of data points.

The invention also provides a method of identifying an item of clothing or footwear by a tag secured thereto, comprising: exposing the tag to coherent radiation; collecting a set of data points that measure scatter of the coherent radiation from intrinsic structure of the tag; and determining a signature of the tag from the set of data points. The tag may be the normal unmodified brand tag, e.g. plastic, cardboard, attached to the clothing or footwear.

The invention also provides a method of identifying a disk, such as a CD or DVD, comprising: exposing the disk to coherent radiation; collecting a set of data points that measure scatter of the coherent radiation from the disk; and determining a signature of the disk from the set of data points.

In summary, the signature can in some cases be obtained from something ancillary to a vendable product, such as its packaging, and in other cases obtained from the object itself, such as from surface structure of a document, or a vendable product. The invention may find many practical applications, for example to control grey market importation or counterfeiting. For such applications, portable readers could be used by customs officers or trading standards officers.

The signature is envisaged to be a digital signature in most applications. Typical sizes of the digital signature with current technology would be in the range 200 bits to 8 k bits, where currently it is preferable to have a digital signature size of about 2 k bits for high security.

Another aspect of the invention provides a method of labelling an article with a signature characteristic of its intrinsic structure, comprising: obtaining the signature by applying any of the above methods of identification; and marking the article with a label that encodes the signature according to a machine-readable encoding protocol.

The signature is preferably encoded in the label using an asymmetric encryption algorithm. For example, the label may represent a cryptogram decipherable by a public key in a public key/private key encryption system. Alternatively, the signature may be encoded in the label using a symmetric encryption algorithm.

It is highly convenient for many materials, especially paper and cardboard, if the label is an ink label applied with a printing process.

The label may be visible, e.g. a bar code, or invisible, e.g. embodied as data in a smart chip when the article is a smart card.

The invention also relates to an article labelled according to the above labelling method.

BRIEF DESCRIPTION OF THE DRAWINGS

For a better understanding of the invention and to show how the same may be carried into effect reference is now made by way of example to the accompanying drawings in which.

DETAILED DESCRIPTION

Figure 1:
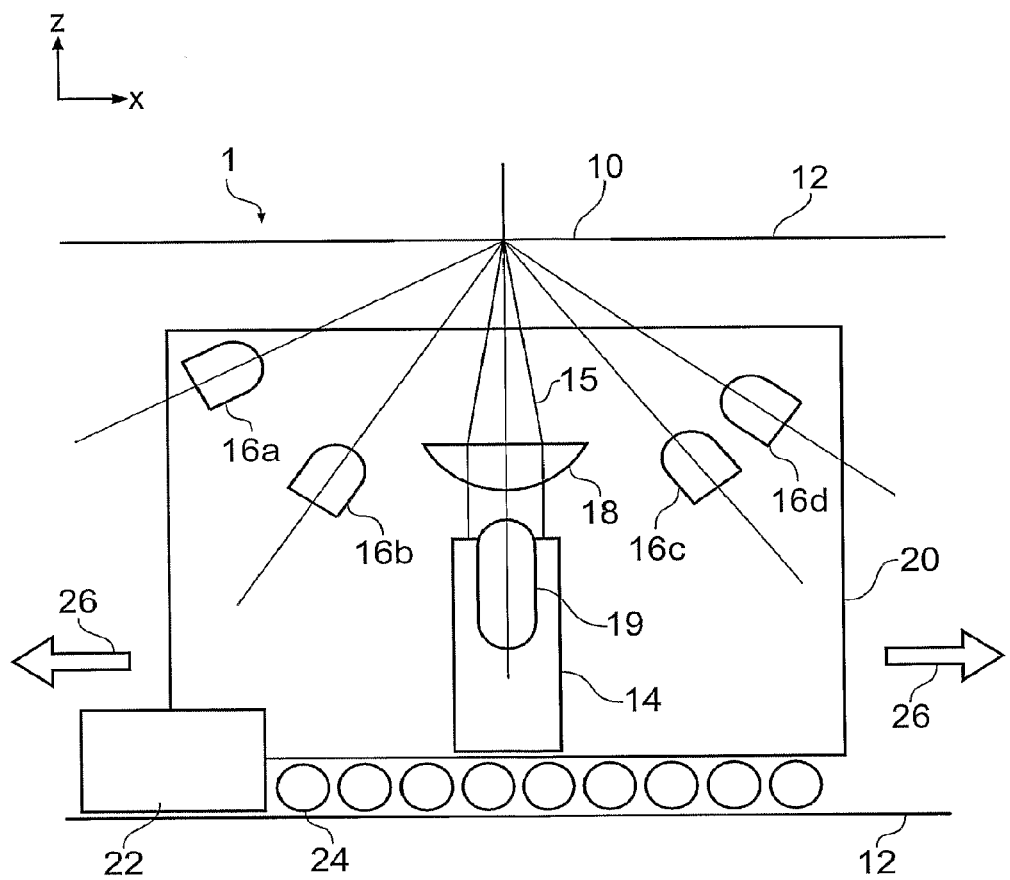
FIG. 1 is a schematic side view of a reader apparatus embodying the invention.

FIG. 1 is a schematic side view of a reader apparatus 1 embodying the invention. The optical reader apparatus 1 is for measuring a signature from an article (not shown) arranged in a reading volume of the apparatus. The reading volume is formed by a reading aperture 10 which is a slit in a housing 12. The housing 12 contains the main optical components of the apparatus. The slit has its major extent in the x direction (see inset axes in the drawing). The principal optical components are a laser source 14 for generating a coherent laser beam 15 and a detector arrangement 16 made up of a plurality of k photodetector elements, where k=4 in this example, labelled 16a, 16b, 16c and 16d. The laser beam 15 is focused by a cylindrical lens 18 into an elongate focus extending in the y direction (perpendicular to the plane of the drawing) and lying in the plane of the reading aperture. In an example prototype reader, the elongate focus has a major axis dimension of about 2 mm and a minor axis dimension of about 40 micrometers. These optical components are contained in a subassembly 20. In the illustrated embodiment, the four detector elements 16a . . . d are distributed either side of the beam axis offset at different angles in an interdigitated arrangement from the beam axis to collect light scattered in reflection from an article present in the reading volume. In an example prototype, the offset angles are −70, −20, +30 and +50 degrees. The angles either side of the beam axis are chosen so as not to be equal so that the data points they collect are as independent as possible. All four detector elements are arranged in a common plane. The photodetector elements 16a . . . d detect light scattered from an article placed on the housing when the coherent beam scatters from the reading volume. As illustrated, the source is mounted to direct the laser beam 15 with its beam axis in the z direction, so that it will strike an article in the reading aperture at normal incidence.

Generally it is desirable that the depth of focus is large, so that any differences in the article positioning in the z direction do not result in significant changes in the size of the beam in the plane of the reading aperture. In an example prototype, the depth of focus is approximately 0.5 mm which is sufficiently large to produce good results. The parameters, of depth of focus, numerical aperture and working distance are interdependent, resulting in a well known trade off between spot size and depth of focus.

A drive motor 22 is arranged in the housing 12 for providing linear motion of the optics subassembly 20 via suitable bearings 24 or other means, as indicated by the arrows 26. The drive motor 22 thus serves to move the coherent beam linearly in the x direction over the reading aperture 10 so that the beam 15 is scanned in a direction transverse to the major axis of the elongate focus. Since the coherent beam 15 is dimensioned at its focus to have a cross-section in the xz plane (plane of the drawing) that is much smaller than a projection of the reading volume in a plane normal to the coherent beam, i.e. in the plane of the housing wall in which the reading aperture is set, a scan of the drive motor 22 will cause the coherent beam 15 to sample many different parts of the reading volume under action of the drive motor 22.

Figure 2:
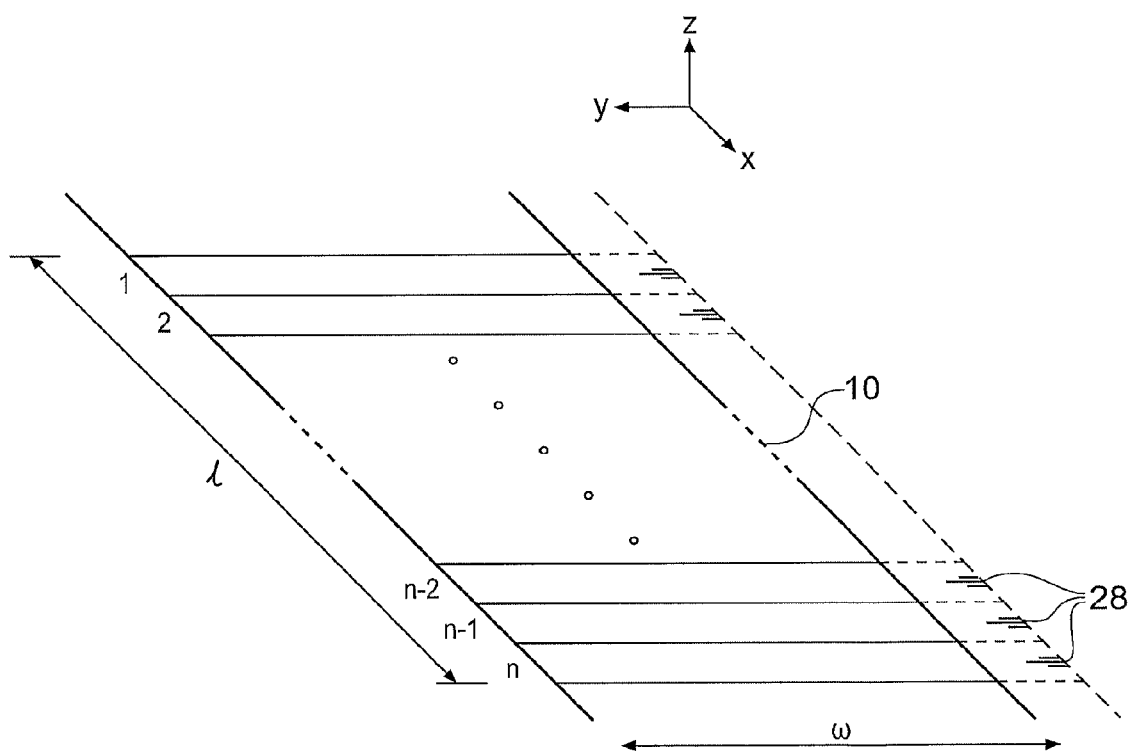
FIG. 2 is a schematic perspective view showing how the reading volume of the reader apparatus is sampled n times by scanning an elongate beam across it.

FIG. 2 is included to illustrate this sampling and is a schematic perspective view showing how the reading area is sampled n times by scanning an elongate beam across it. The sampling positions of the focused laser beam as it is scanned along the reading aperture under action of the drive is represented by the adjacent rectangles numbered 1 to n which sample an area of length 'l' and width 'w'. Data collection is made so as to collect signal at each of the n positions as the drive is scanned along the slit. Consequently, a sequence of k×n data points are collected that relate to scatter from the n different illustrated parts of the reading volume. Also illustrated schematically are distance marks 28 formed on the underside of the housing 12 adjacent the slit 10 along the x direction, i.e. the scan direction. An example spacing between the marks in the x-direction is 300 micrometers.

These marks are sampled by a tail of the elongate focus and provide for linearisation of the data in the x direction, as is described in more detail further below. The measurement is performed by an additional phototransistor 19 which is a directional detector arranged to collect light from the area of the marks 28 adjacent the slit.

In an alternative embodiment, the marks 28 are read by a dedicated encoder emitter/detector module 19 that is part of the optics subassembly 20. Encoder emitter/detector modules are used in bar code readers. For example, we have used an Agilent HEDS-1500 module that is based on a focused light emitting diode (LED) and photodetector. The module signal is fed into the PIC ADC as an extra detector channel.

With an example minor dimension of the focus of 40 micrometers, and a scan length in the x direction of 2 cm, n=500, giving 2000 data points with k=4. A typical range of values for k×n depending on desired security level, article type, number of detector channels 'k' and other factors is expected to be 100<k×n<10,000. It has also been found that increasing the number of detectors k also improves the insensitivity of the measurements to surface degradation of the article through handling, printing etc. In practice, with the prototypes used to date, a rule of thumb is that the total number of independent data points, i.e. k×n, should be 500 or more to give an acceptably high security level with a wide variety of surfaces.

Figure 3:
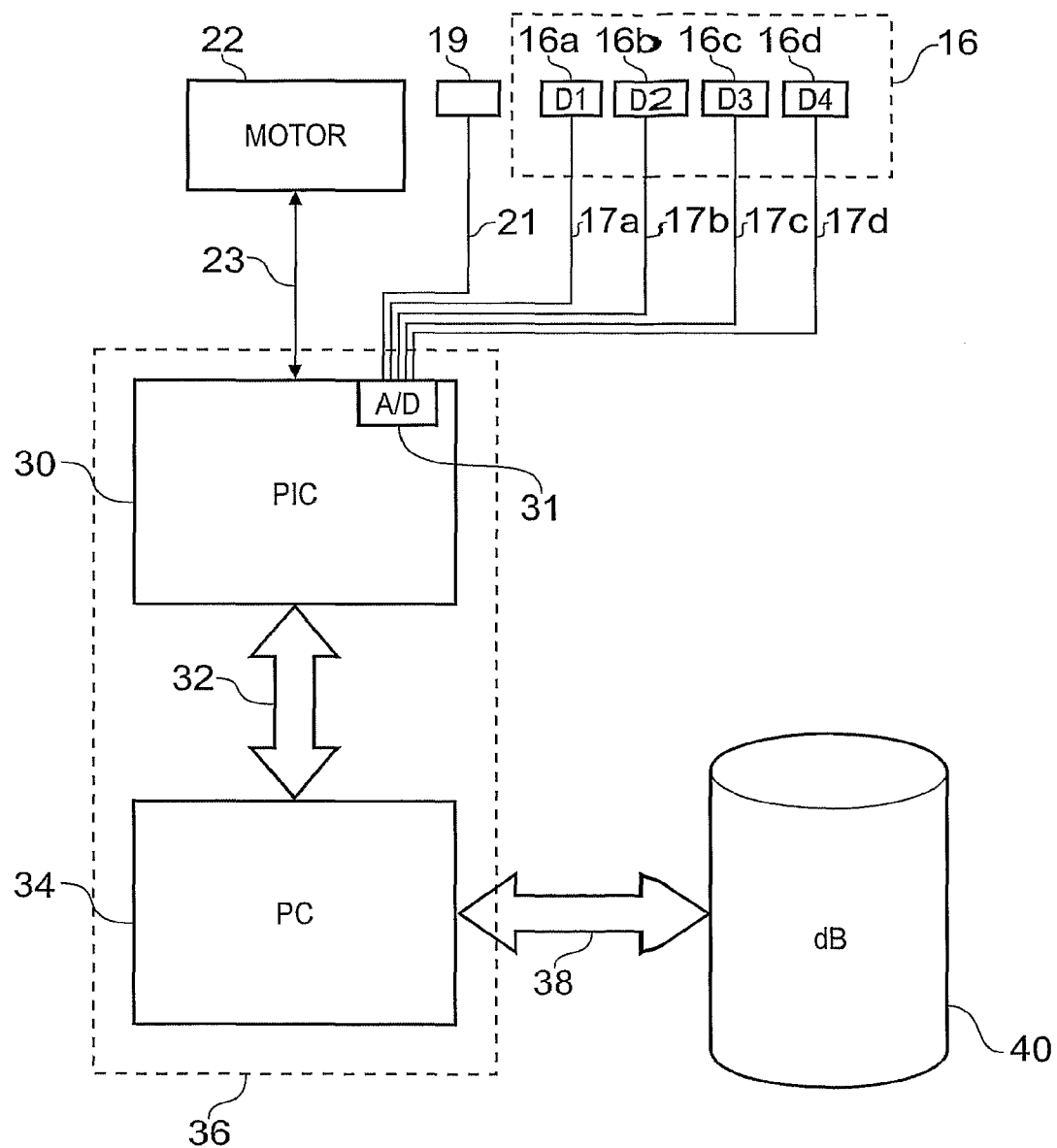
FIG. 3 is a block schematic diagram of the functional components of the reader apparatus.

FIG. 3 is a block schematic diagram of the functional components of the reader apparatus. The motor 22 is connected to a programmable interrupt controller (PIC) 30 through an electrical link 23. The detectors 16a . . . d of the detector module 16 are connected through respective electrical connection lines 17a . . . d to an analogue-to-digital converter (ADC) that is part of the PIC 30. A similar electrical connection line 21 connects the marker reading detector 19 to the PIC 30. It will be understood that optical or wireless links may be used instead of, or in combination with, electrical links. The PIC 30 is interfaced with a personal computer (PC) 34 through a serial connection 32. The PC 34 may be a desktop or a laptop. As an alternative to a PC, other intelligent devices may be used, for example a personal digital assistant (PDA) or a dedicated electronics unit. The PIC 30 and PC 34 collectively form a data acquisition and processing module 36 for determining a signature of the article from the set of data points collected by the detectors 16a . . . d. The PC 34 has access through an interface connection 38 to a database (dB) 40. The database 40 may be resident on the PC 34 in memory, or stored on a drive thereof. Alternatively, the database 40 may be remote from the PC 34 and accessed by wireless communication, for example using mobile telephony services or a wireless local area network (LAN) in combination with the internet. Moreover, the database 40 may be stored locally on the PC 34, but periodically downloaded from a remote source.

The database 40 contains a library of previously recorded signatures. The PC 34 is programmed so that in use it accesses the database 40 and performs a comparison to establish whether the database 40 contains a match to the signature of the article that has been placed in the reading volume. The PC 34 may also be programmed to allow a signature to be added to the database if no match is found. This mode of use is reserved for use by authorised users and may be omitted from systems that are to be used in the field exclusively for verification purposes.

Figure 4:
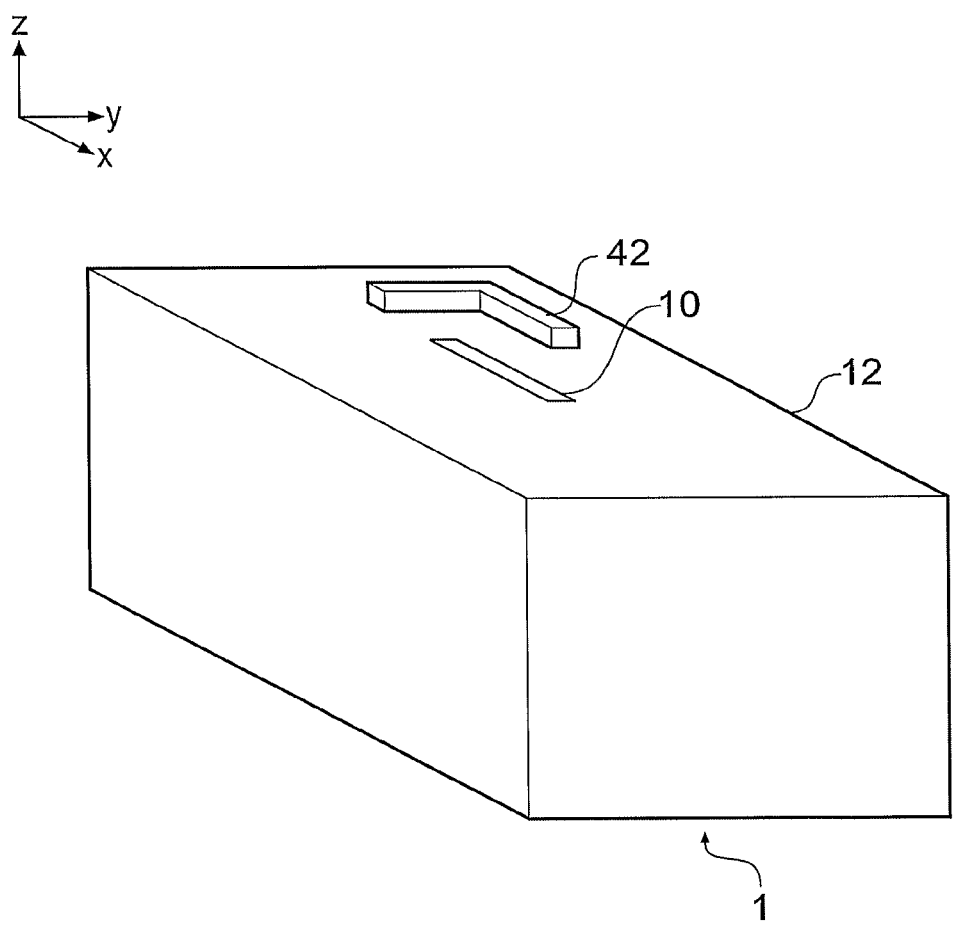
FIG. 4 is a perspective view of the reader apparatus showing its external form.

FIG. 4 is a perspective view of the reader apparatus 1 showing its external form. The housing 12 and slit-shaped reading aperture 10 are evident. A physical location aid 42 is also apparent and is provided for positioning an article of a given form in a fixed position in relation to the reading aperture 10. In the illustrated example, the physical location aid 42 is in the form of a right-angle bracket in which the corner of a document or packaging box can be located. This ensures that the same part of the article can be positioned in the reading aperture 10 whenever the article needs to be scanned. A simple angle bracket or equivalent, is sufficient for articles with a well-defined corner, such as sheets of paper, passports, ID cards and packaging boxes.

A document feeder could be provided to ensure that the article placement was consistent. For example, the apparatus could follow any conventional format for document scanners, photocopiers or document management systems. For packaging boxes, an alternative would be to provide a suitable guide hole, for example a rectangular cross-section hole for accepting the base of a rectangular box or a circular cross-section hole for accepting the base of a tubular box (i.e. cylindrical box).

Figure 5:
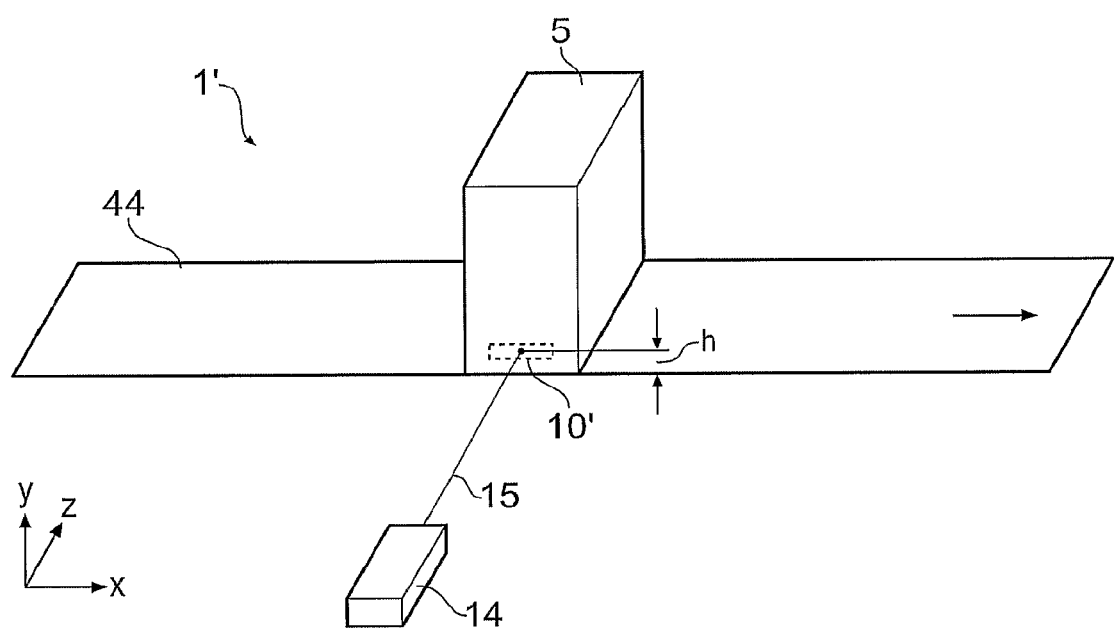
FIG. 5 is a schematic perspective view of an alternative embodiment of the reader apparatus.

FIG. 5 is a schematic perspective view of an alternative embodiment showing a reader apparatus 1' intended for screening batches of articles. The reader is based on a conveyor belt 44 on which articles of packaging can be placed, only one article 5 being illustrated for simplicity of representation. A reading area 10' on the article 5 is scanned by a static laser beam 15 as the article 5 passes on the conveyor belt 44. The laser beam 15 is generated by a laser source 14 arranged fixed in position beside the conveyor belt 44. The laser source 14 has an integral beam focusing lens (not shown) for producing a pencil-like near-collimated beam that travels in the z direction (i.e. horizontal to the floor) to pass over the conveyor belt 44 at a height 'h', thereby intersecting with the article 5 at a height 'h' to scan over the reading area 10'. The beam cross-section may be a spot, i.e. circular (e.g. produced with integral spherical lens), or a line extending in the y direction (e.g. produced with integral cylindrical lens). Although only one article is shown, it will be appreciated that a stream of similar articles can be conveyed and scanned in succession as they pass through the beam 15.

The functional components of the conveyor-based reader apparatus are similar to those of the stand-alone reader apparatus described further above. The only difference of substance is that the article is moved rather than the laser beam, in order to generate the desired relative motion between scan beam and article.

It is envisaged that the conveyor-based reader can be used in a production line or warehouse environment for populating a database with signatures by reading a succession of articles. As a control, each article may be scanned again to verify that the recorded signature can be verified. This could be done with two systems operating in series, or one system through which each article passes twice. Batch scanning could also be applied at point of sale (POS), or using a reader apparatus that was based on POS equipment components.

The above-described embodiments are based on localised excitation with a coherent light beam of small cross-section in combination with detectors that accept light signal scattered over a much larger area that includes the local area of excitation. It is possible to design a functionally equivalent optical system which is instead based on directional detectors that collect light only from localised areas in combination with excitation of a much larger area.

Figure 6A:
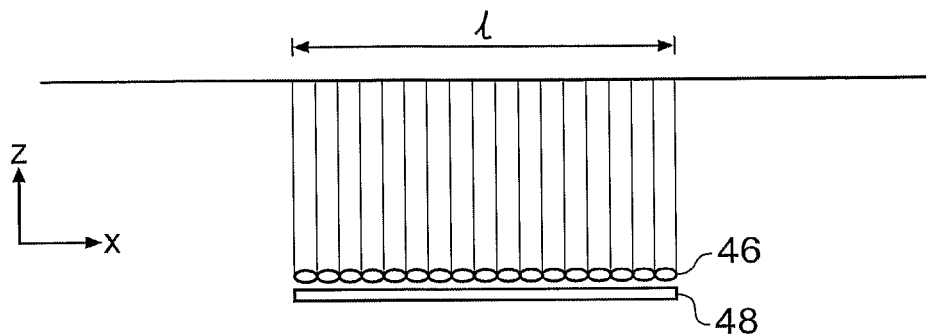
FIG. 6A shows schematically in side view an alternative imaging arrangement for a reader embodying the invention based on directional light collection and blanket illumination.

FIG. 6A shows schematically in side view such an imaging arrangement for a reader embodying the invention which is based on directional light collection and blanket illumination with a coherent beam. An array detector 48 is arranged in combination with a cylindrical microlens array 46 so that adjacent strips of the detector array 48 only collect light from corresponding adjacent strips in the reading volume. With reference to FIG. 2, each cylindrical microlens is arranged to collect light signal from one of the n sampling strips. The coherent illumination can then take place with blanket illumination of the whole reading volume (not shown in the illustration).

A hybrid system with a combination of localised excitation and localised detection may also be useful in some cases.

Figure 6B:
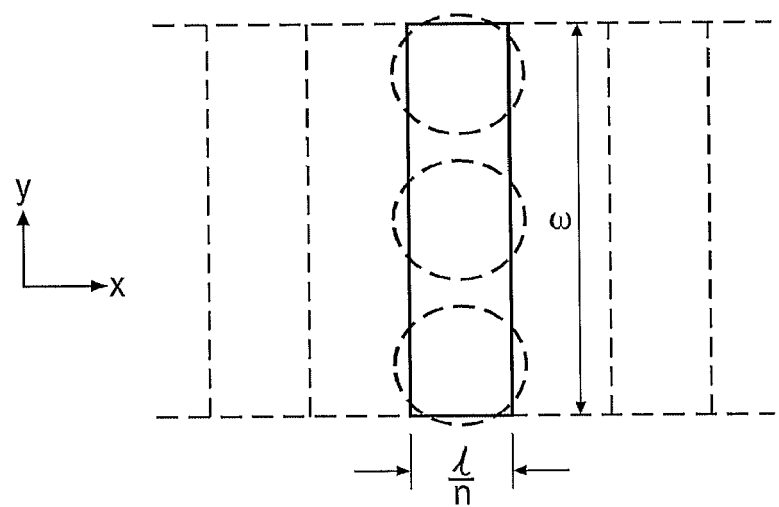
FIG. 6B shows schematically in plan view the optical footprint of a further alternative imaging arrangement for a reader embodying the invention in which directional detectors are used in combination with localised illumination with an elongate beam.

FIG. 6B shows schematically in plan view the optical footprint of such a hybrid imaging arrangement for a reader embodying the invention in which directional detectors are used in combination with localised illumination with an elongate beam. This embodiment may be considered to be a development of the embodiment of FIG. 1 in which directional detectors are provided. In this embodiment three banks of directional detectors are provided, each bank being targeted to collect light from different portions along the 'l×w' excitation strip. The collection area from the plane of the reading volume are shown with the dotted circles, so that a first bank of, for example 2, detectors collects light signal from the upper portion of the excitation strip, a second bank of detectors collects light signal from a middle portion of the excitation strip and a third bank of detectors collects light from a lower portion of the excitation strip. Each bank of detectors is shown having a circular collection area of diameter approximately 1/m, where m is the number of subdivisions of the excitation strip, where m=3 in the present example. In this way the number of independent data points can be increased by a factor of m for a given scan length 1. As described further below, one or more of different banks of directional detectors can be used for a purpose other than collecting light signal that samples a speckle pattern. For example, one of the banks may be used to collect light signal in a way optimised for barcode scanning. If this is the case it will generally be sufficient for that bank to contain only one detector, since there will be no advantage obtaining cross-correlations when only scanning for contrast.

Having now described the principal structural components and functional components of various reader apparatuses suitable for carrying out the invention, the numerical processing used to determine a signature is now described. It will be understood that this numerical processing is implemented for the most part in a computer program that runs on the PC 34 with some elements subordinated to the PIC 30.

Figure 7:
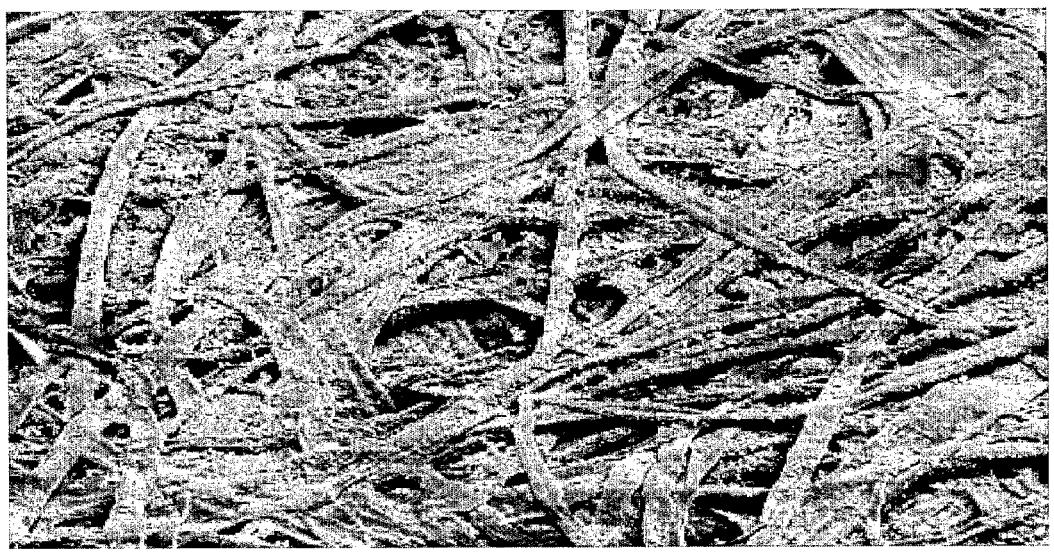
FIG. 7 is a microscope image of a paper surface with the image covering an area of approximately 0.5×0.2 mm.

FIG. 7 is a microscope image of a paper surface with the image covering an area of approximately 0.5×0.2 mm. This figure is included to illustrate that macroscopically flat surfaces, such as from paper, are in many cases highly structured at a microscopic scale. For paper, the surface is microscopically highly structured as a result of the intermeshed network of wood fibres that make up paper. The figure is also illustrative of the characteristic length scale for the wood fibres which is around 10 microns. This dimension has the correct relationship to the optical wavelength of the coherent beam to cause diffraction and hence speckle, and also diffuse scattering which has a profile that depends upon the fibre orientation. It will thus be appreciated that if a reader is to be designed for a specific class of goods, the wavelength of the laser can be tailored to the structure feature size of the class of goods to be scanned. It is also evident from the figure that the local surface structure of each piece of paper will be unique in that it depends on how the individual wood fibres are arranged. A piece of paper is thus no different from a specially created token, such as the special resin tokens or magnetic material deposits of the prior art, in that it has structure which is unique as a result of it being made by a process governed by laws of nature. The same applies to many other types of article.

In other words, the inventor has discovered that it is essentially pointless to go to the effort and expense of making specially prepared tokens, when unique characteristics are measurable in a straightforward manner from a wide variety of every day articles. The data collection and numerical processing of a scatter signal that takes advantage of the natural structure of an article's surface (or interior in the case of transmission) is now described.

Figure 8A:
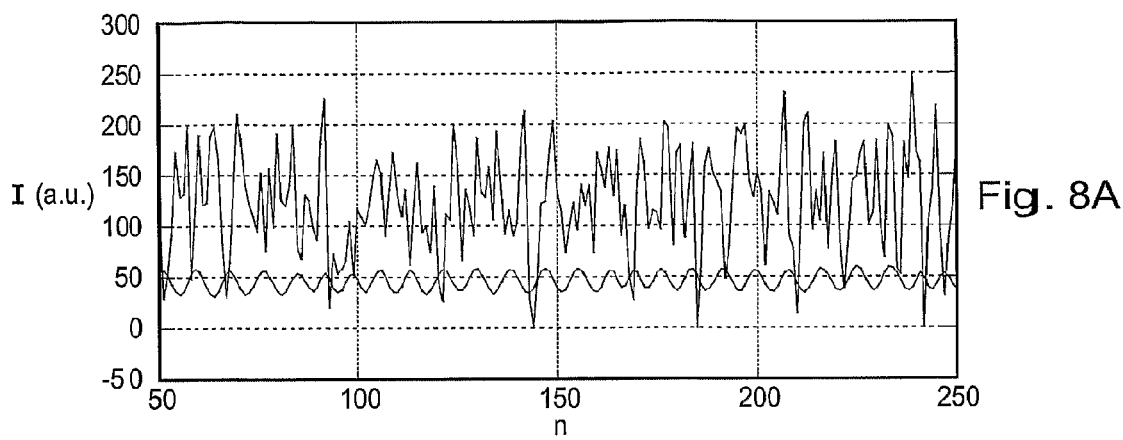
FIG. 8A shows raw data from a single photodetector using the reader of FIG. 1 which consists of a photodetector signal and an encoder signal.

FIG. 8A shows raw data from a single one of the photodetectors 16a . . . d of the reader of FIG. 1. The graph plots signal intensity I in arbitrary units (a.u.) against point number n (see FIG. 2). The higher trace fluctuating between I=0-250 is the raw signal data from photodetector 16a. The lower trace is the encoder signal picked up from the markers 28 (see FIG. 2) which is at around I=50.

Figure 8B:
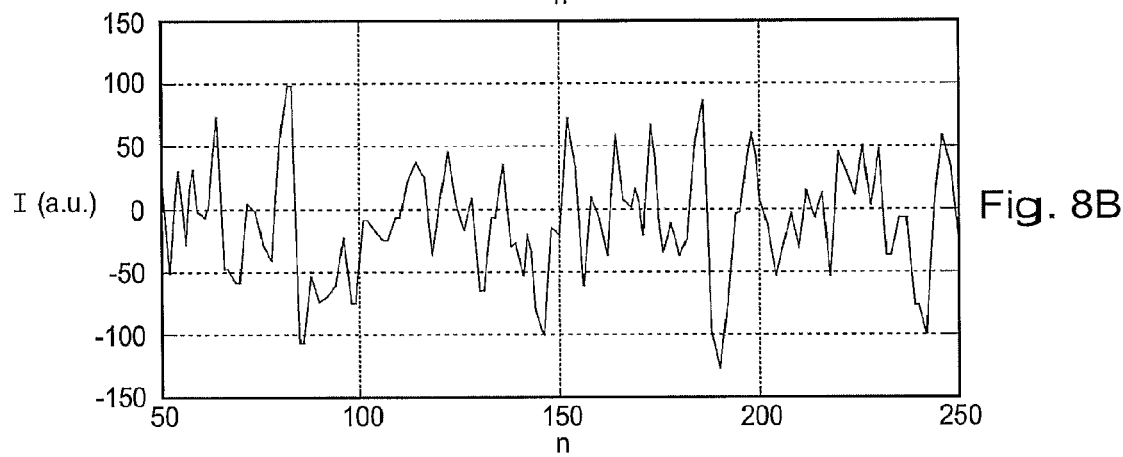
FIG. 8B shows the photodetector data of FIG. 8A after linearisation with the encoder signal and averaging the amplitude.

FIG. 8B shows the photodetector data of FIG. 8A after linearisation with the encoder signal (n.b. although the x axis is on a different scale from FIG. 8A, this is of no significance). In addition, the average of the intensity has been computed and subtracted from the intensity values. The processed data values thus fluctuate above and below zero.

Figure 8C:
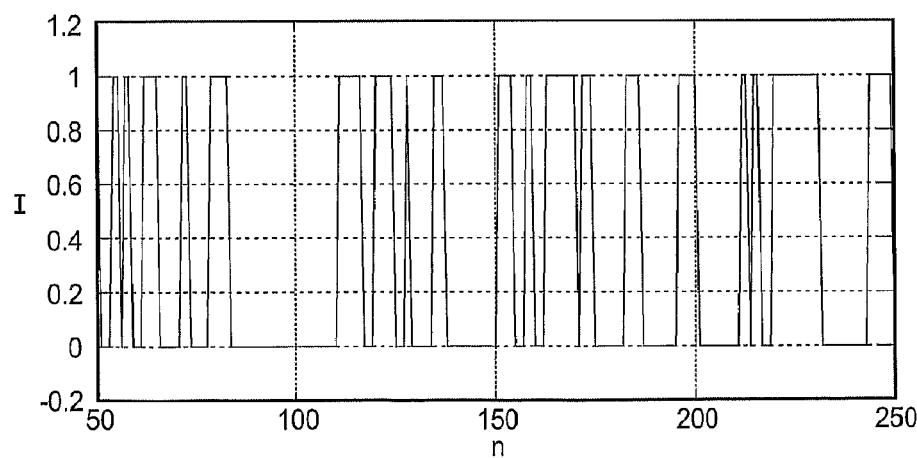
FIG. 8C shows the data of FIG. 8B after digitisation according to the average level.

FIG. 8C shows the data of FIG. 8B after digitisation. The digitisation scheme adopted is a simple binary one in which any positive intensity values are set at value 1 and any negative intensity values are set at zero. It will be appreciated that multi-state digitisation could be used instead, or any one of many other possible digitisation approaches. The main important feature of the digitisation is merely that the same digitisation scheme is applied consistently.

Figure 9:
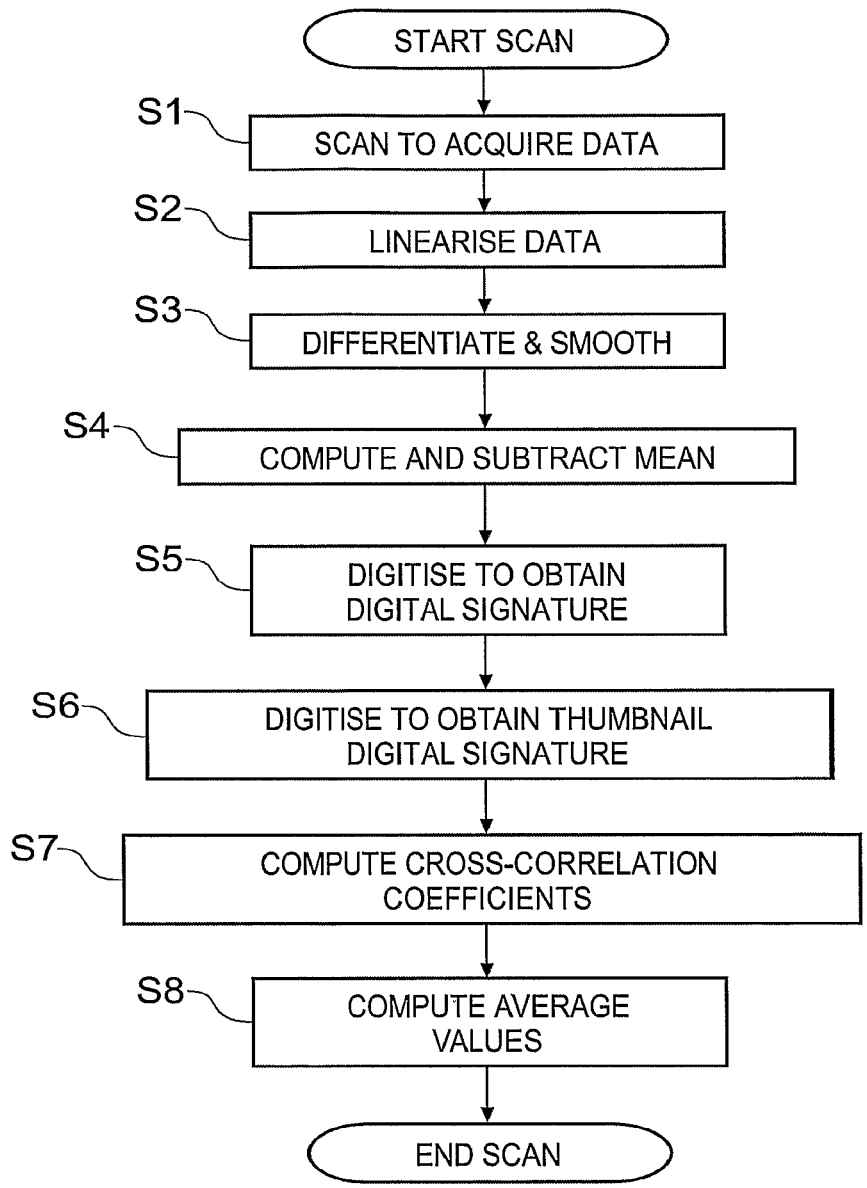
FIG. 9 is a flow diagram showing how a signature of an article is generated from a scan.

FIG. 9 is a flow diagram showing how a signature of an article is generated from a scan.

Step S1 is a data acquisition step during which the optical intensity at each of the photodetectors is acquired approximately every 1 ms during the entire length of scan. Simultaneously, the encoder signal is acquired as a function of time. It is noted that if the scan motor has a high degree of linearisation accuracy (e.g. as would a stepper motor) then linearisation of the data may not be required. The data is acquired by the PIC 30 taking data from the ADC 31. The data points are transferred in real time from the PIC 30 to the PC 34. Alternatively, the data points could be stored in memory in the PIC 30 and then passed to the PC 34 at the end of a scan. The number n of data points per detector channel collected in each scan is defined as N in the following. Further, the value $a_k(i)$ is defined as the i-th stored intensity value from photodetector k, where i runs from 1 to N. Examples of two raw data sets obtained from such a scan are illustrated in FIG. 8A.

Step S2 uses numerical interpolation to locally expand and contract $a_k(i)$ so that the encoder transitions are evenly spaced in time. This corrects for local variations in the motor speed. This step is performed in the PC 34 by a computer program.

Step S3 is an optional step. If performed, this step numerically differentiates the data with respect to time. It may also be desirable to apply a weak smoothing function to the data. Differentiation may be useful for highly structured surfaces, as it serves to attenuate uncorrelated contributions from the signal relative to correlated (speckle) contributions.

Step S4 is a step in which, for each photodetector, the mean of the recorded signal is taken over the N data points. For each photodetector, this mean value is subtracted from all of the data points so that the data are distributed about zero intensity. Reference is made to FIG. 8B which shows an example of a scan data set after linearisation and subtraction of a computed average.

Step S5 digitises the analogue photodetector data to compute a digital signature representative of the scan. The digital signature is obtained by applying the rule: $a_k(i)>0$ maps onto binary '1' and $a_k(i)<=0$ maps onto binary '0'. The digitised data set is defined as $d_k(i)$ where i runs from 1 to N. The signature of the article may advantageously incorporate further components in addition to the digitised signature of the intensity data just described. These further optional signature components are now described.

Step S6 is an optional step in which a smaller 'thumbnail' digital signature is created. This is done either by averaging together adjacent groups of in readings, or more preferably by picking every cth data point, where c is the compression factor of the thumbnail. The latter is preferred since averaging may disproportionately amplify noise. The same digitisation rule used in Step S5 is then applied to the reduced data set. The thumbnail digitisation is defined as $t_k(i)$ where i runs 1 to N/c and c is the compression factor.

Step S7 is an optional step applicable when multiple detector channels exist. The additional component is a cross-correlation component calculated between the intensity data obtained from different ones of the photodetectors. With 2 channels there is one possible cross-correlation coefficient, with 3 channels up to 3, and with 4 channels up to 6 etc. The cross-correlation coefficients are useful, since it has been found that they are good indicators of material type. For example, for a particular type of document, such as a passport of a given type, or laser printer paper, the cross-correlation coefficients always appear to lie in predictable ranges. A normalised cross-correlation can be calculated between $a_k(i)$ and $a_l(i)$, where k≠l and k,l vary across all of the photodetector channel numbers. The normalised cross-correlation function Γ is defined as $$\Gamma(k,l) = \frac{\sum_{i=1}^{N} a_k(i)a_l(i)}{\sqrt{\left(\sum_{i=1}^{N} a_k(i)^2\right)\left(\sum_{i=1}^{N} a_l(i)^2\right)}}$$

Another aspect of the cross-correlation function that can be stored for use in later verification is the width of the peak in the cross-correlation function, for example the full width half maximum (FWHM). The use of the cross-correlation coefficients in verification processing is described further below.

Step S8 is another optional step which is to compute a simple intensity average value indicative of the signal intensity distribution. This may be an overall average of each of the mean values for the different detectors or an average for each detector, such as a root mean square (rms) value of $a_k(i)$. If the detectors are arranged in pairs either side of normal incidence as in the reader described above, an average for each pair of detectors may be used. The intensity value has been found to be a good crude filter for material type, since it is a simple indication of overall reflectivity and roughness of the sample. For example, one can use as the intensity value the unnormalised rms value after removal of the average value, i.e. the DC background.

The signature data obtained from scanning an article can be compared against records held in a signature database for verification purposes and/or written to the database to add a new record of the signature to extend the existing database.

A new database record will include the digital signature obtained in Step S5 as well as optionally its smaller thumbnail version obtained in Step S6 for each photodetector channel, the cross-correlation coefficients obtained in Step S7 and the average value(s) obtained in Step S8. Alternatively, the thumbnails may be stored on a separate database of their own optimised for rapid searching, and the rest of the data (including the thumbnails) on a main database.

Figure 10:
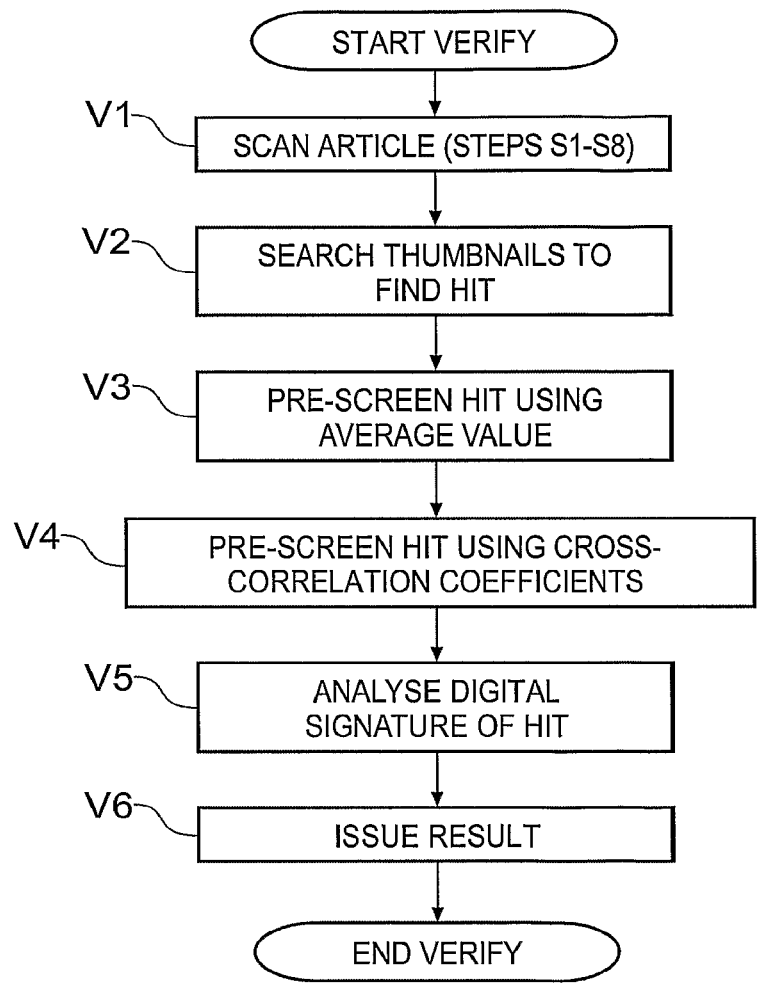
FIG. 10 is a flow diagram showing how a signature of an article obtained from a scan can be verified against a signature database.

FIG. 10 is a flow diagram showing how a signature of an article obtained from a scan can be verified against a signature database.

In a simple implementation, the database could simply be searched to find a match based on the full set of signature data. However, to speed up the verification process, the process preferably uses the smaller thumbnails and pre-screening based on the computed average values and cross-correlation coefficients as now described.

Verification Step V1 is the first step of the verification process, which is to scan an article according to the process described above, i.e. to perform Scan Steps S1 to S8.

Verification Step V2 takes each of the thumbnail entries and evaluates the number of matching bits between it and $t_k(i+j)$, where j is a bit offset which is varied to compensate for errors in placement of the scanned area. The value of j is determined and then the thumbnail entry which gives the maximum number of matching bits. This is the 'hit' used for further processing.

Verification Step V3 is an optional pre-screening test that is performed before analysing the full digital signature stored for the record against the scanned digital signature. In this pre-screen, the rms values obtained in Scan Step S8 are compared against the corresponding stored values in the database record of the hit. The 'hit' is rejected from further processing if the respective average values do not agree within a pre-defined range. The article is then rejected as non-verified (i.e. jump to Verification Step V6 and issue fail result).

Verification Step V4 is a further optional pre-screening test that is performed before analysing the full digital signature. In this pre-screen, the cross-correlation coefficients obtained in Scan Step S7 are compared against the corresponding stored values in the database record of the hit. The 'hit' is rejected from further processing if the respective cross-correlation coefficients do not agree within a predefined range. The article is then rejected as non-verified (i.e. jump to Verification Step V6 and issue fail result).

Another check using the cross-correlation coefficients that could be performed in Verification Step V4 is to check the width of the peak in the cross-correlation function, where the cross-correlation function is evaluated by comparing the value stored from the original scan in Scan Step S7 above and the re-scanned value:

$$\Gamma_{k,l}(j) = \frac{\sum_{i=1}^{N} a_k(i) a_l(i+j)}{\sqrt{\left(\sum_{i=1}^{N} a_k(i)^2\right)\left(\sum_{i=1}^{N} a_l(i)^2\right)}}$$

If the width of the re-scanned peak is significantly higher than the width of the original scan, this may be taken as an indicator that the re-scanned article has been tampered with or is otherwise suspicious. For example, this check should beat a fraudster who attempts to fool the system by printing a bar code or other pattern with the same intensity variations that are expected by the photodetectors from the surface being scanned.

Verification Step V5 is the main comparison between the scanned digital signature obtained in Scan Step S5 and the corresponding stored values in the database record of the hit. The full stored digitised signature, $d_k^{db}(i)$ is split into n blocks of q adjacent bits on k detector channels, i.e. there are qk bits per block. A typical value for q is 4 and a typical value for k is 4, making typically 16 bits per block. The qk bits are then matched against the qk corresponding bits in the stored digital signature $d_k^{db}(i+j)$. If the number of matching bits within the block is greater or equal to some pre-defined threshold $z_{thresh}$, then the number of matching blocks is incremented. A typical value for $z_{thresh}$ is 13. This is repeated for all n blocks. This whole process is repeated for different offset values of j, to compensate for errors in placement of the scanned area, until a maximum number of matching blocks is found. Defining M as the maximum number of matching blocks, the probability of an accidental match is calculated by evaluating:

$$p(M) = \sum_{w=n-M}^{n} s^w (1-s)^{n-w} {}_n C_w$$

where s is the probability of an accidental match between any two blocks (which in turn depends upon the chosen value of $z_{threshold}$), M is the number of matching blocks and p(M) is the probability of M or more blocks matching accidentally. The value of is determined by comparing blocks within the data base from scans of different objects of similar materials, e.g. a number of scans of paper documents etc. For the case of q=4, k=4 and $z_{threshold}$=13, we find a typical value of s is 0.1. If the qk bits were entirely independent, then probability theory would give s=0.01 for $z_{threshold}$=13. The fact that we find a higher value empirically is because of correlations between the k detector channels and also correlations between adjacent bits in the block due to a finite laser spot width. A typical scan of a piece of paper yields around 314 matching blocks out of a total number of 510 blocks, when compared against the data base entry for that piece of paper. Setting M=314, n=510, s=0.1 for the above equation gives a probability of an accidental match of $10^{-177}$.

Verification Step V6 issues a result of the verification process. The probability result obtained in Verification Step V5 may be used in a pass/fail test in which the benchmark is a pre-defined probability threshold. In this case the probability threshold may be set at a level by the system, or may be a variable parameter set at a level chosen by the user. Alternatively, the probability result may be output to the user as a confidence level, either in raw form as the probability itself, or in a modified form using relative terms (e.g. no match/poor match/good match/excellent match) or other classification.

It will be appreciated that many variations are possible. For example, instead of treating the cross-correlation coefficients as a pre-screen component, they could be treated together with the digitised intensity data as part of the main signature. For example the cross-correlation coefficients could be digitised and added to the digitised intensity data. The cross-correlation coefficients could also be digitised on their own and used to generate bit strings or the like which could then be searched in the same way as described above for the thumbnails of the digitised intensity data in order to find the hits.

A further implementation of the invention is now described.

Figure 11:
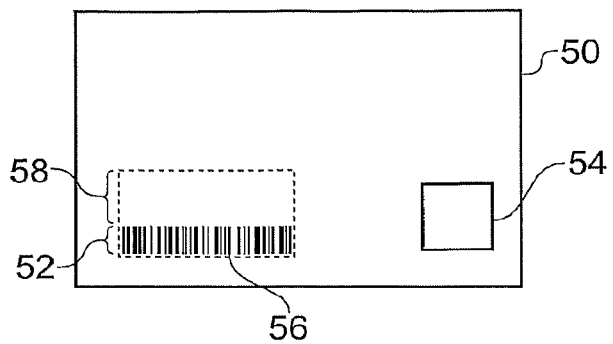
FIG. 11 is a schematic plan view of an ID card bearing a barcode label that encodes a digital signature obtained from an intrinsic measured surface characteristic.

FIG. 11 shows an ID card 50 bearing a barcode. The ID card may also bear an independent security element 54 such as a photograph, hologram or contain some biometric information specific to an individual. The barcode is shown as part of a scan area 56. This is illustrated with a dashed line, since it is featureless on the ID card. The scan area is subdivided between a lower area 52 containing the barcode and a blank upper area 58. The ID card 50 is designed to be scanned by a reader apparatus of the kind illustrated in FIG. 6B, where one of the directional detector banks is used to scan the barcode area 52 and the other two banks to scan the upper area 58. In this embodiment, the barcode encodes the signature obtained by scanning the blank upper area using the method of the invention.

In other words, the barcode was originally applied at the time of manufacture of the ID card by scanning the blank upper area of the card according to the method of the invention and then printing the barcode onto the lower area 52. The ID card is thus labelled with a signature characteristic of its intrinsic structure, namely the surface structure in the upper area 58.

It is noted that the barcode may itself be used for linearisation of the scan instead of or in combination with the separate linearisation marks described above. This may be especially useful when the reader has a drive with poor linearity, such as a roller drive of the kind used in automated telling machines (ATMs) for example. Tolerance to drives with poor linearity will allow a reader to be incorporated in many card reading devices such as ATMs with minimum modification. Indeed, a barcode, or even dummy markings, may be printed on the card solely for the purpose of linearisation and not used for the encryption at all. In that case, verification could be performed using reference to a database or by taking data from another part of the card, for example by taking data from a chip (so-called smart card).

It will be appreciated that this basic approach can be used to mark a wide variety of articles with a label that encodes the articles own signature obtained from its intrinsic physical properties, for example any printable article, including paper or cardboard articles or plastic articles.

Given the public nature of the barcode or other label that follows a publicly known encoding protocol, it is advisable to make sure that the signature has been transformed using an asymmetric encryption algorithm for creation of the barcode, i.e. a one-way function is used, such as according to the well known RSA algorithm. A preferred implementation is for the label to represent a public key in a public key/private key encryption system. If the system is used by a number of different customers, it is advisable that each customer has its own private key, so that disclosure of a private key will only affect one customer. The label thus encodes the public key and the private key is located securely with the authorised persons.

Alternatively, the encryption could be symmetric. In this case the key could be held securely in tamper-proof memory or crypto-processor smart cards on the document scanners.

A further perceived advantage of the labelling approach is that a novice user would be unaware of the verification being carried out without special knowledge. It would be natural for the user to assume that the reader apparatus was simply a barcode scanner, and it was the barcode that was being scanned.

In one example, for CD's, DVD's or other content bearing disks, the signature is on the disk and forms part of a decryption key for the data on the disk. The disk player then reads the speckle signature from the disk when reading the data.

The labelling scheme could be used to allow articles to be verified without access to a database purely on the basis of the label. This is a similar approach conceptually to the failed banknote scheme reported in the prior art [4].

However, it is also envisaged that the labelling scheme could be used in combination with a database verification scheme. For example, the barcode could encode a thumbnail form of the digital signature and be used to allow a rapid pre-screen prior to screening with reference to a database. This could be a very important approach in practice, since potentially in some database applications, the number of records could become huge (e.g. millions) and searching strategies would become critical. Intrinsically high speed searching techniques, such as the use of bitstrings, could become important As an alternative to the barcode encoding a thumbnail, the barcode (or other label) could encode a record locator, i.e. be an index or bookmark, which can be used to rapidly find the correct signature in the database for further comparison.

Another variant is that the barcode (or other label) encodes a thumbnail signature which can be used to get a match with reasonable but not high confidence if a database is not available (e.g. temporarily off-line, or the scanning is being done in an unusually remote location without internet access). That same thumbnail can then be used for rapid record locating within the main database if the database is available, allowing a higher confidence verification to be performed.

Figure 12:
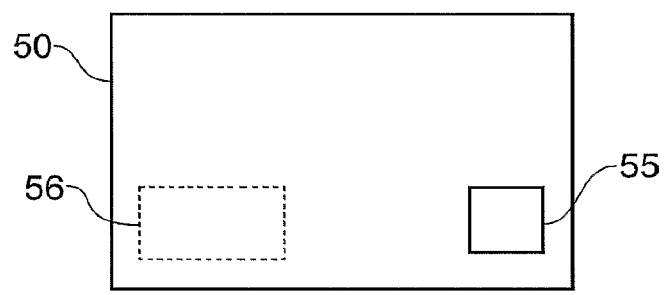
FIG. 12 is a schematic plan view of an ID card with a chip carrying data that encodes a digital signature obtained from an intrinsic measured surface characteristic.

FIG. 12 is a schematic plan view of an ID card 50 which is a so-called smart card that incorporates a data carrying chip 54. The data carried by the chip 54 includes signature encoding data that encodes a digital signature obtained from an intrinsic measured surface characteristic of the ID card 50 obtained from a scan area 56 which is featureless in this example as indicated by the dotted lines, but could be decorated in any desired way, or contain a photograph, for example.

Figure 13:
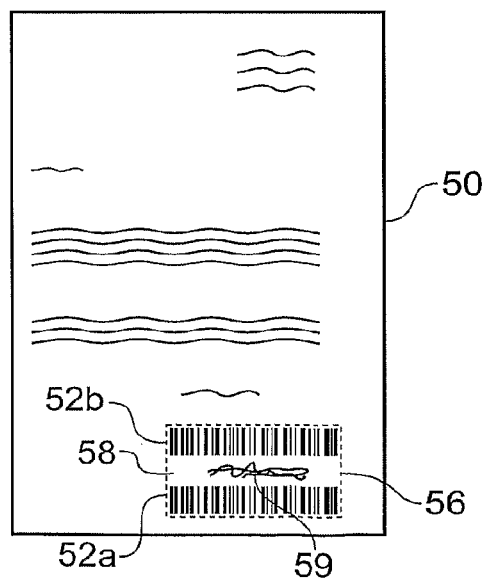
FIG. 13 is a schematic plan view of a warranty document bearing two barcode labels that encode a digital signature obtained from an intrinsic measured surface characteristic.

FIG. 13 is a schematic plan view of a warranty document 50. The scan area 56 includes two barcode labels 52a, 52b arranged one above the other which encode a digital signature obtained from an intrinsic measured surface characteristic, similar to the ID card example of FIG. 11. The barcodes 52a, 52b are arranged above and below a digital signature scan area 58 for a person's signature 59 as schematically illustrated. The area 58 at least is preferably covered with a transparent adhesive covering for tamper protection.

Many other commercial examples will be envisaged, the above FIGS. 11 to 13 given by way of example only.

From the above detailed description it will be understood how an article made of material, such as paper or cardboard, or plastic, can be identified by exposing the material to coherent radiation, collecting a set of data points that measure scatter of the coherent radiation from intrinsic structure of the material, and determining a signature of the article from the set of data points.

It will also be understood that the scan area is essentially arbitrary in terms of its size or location on an article. If desired, the scan could be a linear scan rastered to cover a larger two-dimensional area, for example.

Moreover, it will be understood how this can be applied to identify a product by its packaging, a document or an item of clothing, by exposing the article to coherent radiation, collecting a set of data points that measure scatter of the coherent radiation from intrinsic structure of the article, and determining a signature of the product from the set of data points.

From the above description of the numerical processing, it will be understood that degradation of the beam localisation (e.g. beam cross-section enlargement in the reading volume owing to sub-optimum focus of the coherent beam) will not be catastrophic to the system, but merely degrade its performance by increasing the accidental match probability. The apparatus is thus robust against apparatus variations giving a stable gradual degradation in performance rather than a sudden unstable failure. In any case, it is simple to perform a self test of a reader, thereby picking up any equipment problems, by performing an autocorrelation on the collected data to ascertain the characteristic minimum feature size in the response data.

A further security measure that can be applied to paper or cardboard, for example, is to adhesively bond a transparent seal (e.g. adhesive tape) over the scanned area. The adhesive is selected to be sufficiently strong that its removal will destroy the underlying surface structure which it is essential to preserve in order to perform a verification scan. The same approach can be applied to deposition of transparent polymer or plastic films on a card, or its encapsulation with similar materials.

As described above, the reader may be embodied in an apparatus designed specifically to implement the invention. In other cases, the reader will be designed by adding appropriate ancillary components to an apparatus principally designed with another functionality in mind, such as a photocopier machine, document scanner, document management system, POS device, ATM, air ticket boarding card reader or other device.

Many other variations of the invention will be envisaged by the skilled person in addition to those specifically mentioned above.

REFERENCES

[1] PCT/GB03/03917—Cowburn
[2] GB 2 221 870 A—Ezra, Hare & Pugsley
[3] U.S. Pat. No. 6,584,214—Pappu, Gershenfeld & Smith
[4] Kravolec "Plastic tag makes foolproof ID" Technology Research News, 2 Oct. 2002
[5] R Anderson "Security Engineering: a guide to building dependable distributed systems" Wiley 2001, pages 251-252 ISBN 0-471-38922-6
[6] U.S. Pat. No. 5,521,984
[7] U.S. Pat. No. 5,325,167

The invention claimed is:

1. An apparatus for determining a signature from an article arranged in a reading volume, comprising:
a source for generating a coherent beam;
a detector arrangement for collecting a set of data points from signals obtained when the coherent beam scatters from the intrinsic surface structure of the reading volume, wherein each of the different ones of the data points relates to scatter from a different part of the reading volume; and
a data acquisition and processing module for determining a signature and a thumbnail signature of the article from the set of data points.

2. The apparatus of claim 1, wherein the data acquisition and processing module is configured to determine the thumbnail signature by applying a compression factor.

3. The apparatus of claim 2, wherein the data acquisition and processing module is configured to determine the thumbnail signature by selecting every $c^{th}$ bit from the signature, where c is the compression factor.

4. The apparatus of claim 2, wherein the data acquisition and processing module is configured to determine the thumbnail signature by selecting every $c^{th}$ data point, where c is the compression factor.

5. The apparatus of claim 2, wherein the data acquisition and processing module is configured to determine the thumbnail signature by averaging adjacent groups of data points.

6. The apparatus of claim 1, wherein the data acquisition and processing module is configured to determine the thumbnail signature by averaging adjacent groups of bits of the signature.

7. The apparatus of claim 1, wherein the data acquisition and processing module is further configured to store the digital signature with its thumbnail digital signature in a database.

8. The apparatus of claim 7, wherein the data acquisition and processing module is configured to store the digital signature with its thumbnail digital signature in the database conditional on there being no match between it and any digital signature already stored in the database.

9. The apparatus of claim 7, further comprising:
a database of previously recorded signatures and their thumbnail digital signatures; and
a search tool configured to (i) search the database to seek at least one candidate match by performing a comparison between the determined thumbnail digital signature and the previously recorded thumbnail digital signatures; and (ii) determine for any candidate match whether there is a match by performing a comparison between the determined digital signature and the at least one previously recorded digital signatures.

10. The apparatus of claim 9, wherein the search tool is further configured to determine for each match a confidence level based on degree of similarity between the determined digital signature and the previously recorded digital signature found to have a match.

11. The apparatus of claim 7, wherein the different parts of the reading volume are subjected to coherent light sequentially.

12. The apparatus of claim 1, further comprising a drive means configured to move the coherent beam over the reading volume such that different ones of the data points relate to scatter from different parts of the reading volume, and the coherent beam is dimensioned to have a cross-section substantially smaller than a projection of the reading volume in a plane normal to the coherent beam so that the coherent beam samples different parts of the reading volume under action of the drive means.

13. The apparatus of claim 1, wherein the detector arrangement includes a plurality of detector channels arranged and configured to sense scatter from respective different parts of the reading volume to obtain different ones of the data points that relate to scatter from different parts of the reading volume.

14. The apparatus of claim 1, wherein the detector arrangement comprises a group of detector elements angularly distributed and configured to collect a group of data points for each different part of the reading volume.

15. The apparatus of claim 14, wherein the signature incorporates a contribution from a comparison between data points of the same group.

16. The apparatus of claim 1, wherein the source is mounted to direct the coherent beam onto the reading volume so that it will strike an article with near normal incidence.

17. The apparatus of claim 1, wherein the detector arrangement is arranged in reflection to detect radiation back scattered from the reading volume.

18. A database comprising a plurality of records, each comprising:
a digital signature of an article obtained by digitising a set of data points obtained from the article, the set of data points comprising at least one data point relating to scatter from the intrinsic surface structure of a first point of the article and at least one data point relating to scatter from the intrinsic surface structure of a second point of the article; and
a thumbnail digital signature of the article.

19. The database of claim 18, wherein the data points are obtained from scattering of coherent light from the article.

20. A system comprising a search tool configured to search a database according to claim 18 for candidate matches by performing a comparison between an input thumbnail digital signature and the thumbnail digital signatures held in the database.

21. The system of claim 20 wherein the search tool is further configured to perform a comparison between the input digital signature and the digital signature held in the record of the candidate match to determine for any candidate match whether there is a match.

22. The system of claim 20, wherein the search tool is configured to search the database for candidate matches using an approximate record locator.

23. The system of claim 20, wherein the database is remote from the system.

24. The system of claim 20, wherein the database is integral with the system.

25. A method of scanning an article arranged in a reading volume, the method comprising:
collecting a set of data points, with a detector, from signals obtained when an incident coherent beam scatters from the intrinsic surface structure of the reading volume, wherein each of the different ones of the data points relates to scatter from a different part of the reading volume;
determining a signature of the article from the set of data points with a processor; and determining a thumbnail signature of the article from the set of data points.

26. The method of claim 25, wherein the determining the thumbnail signature comprises applying a compression factor.

27. The method of claim 26, wherein the determining the thumbnail signature comprises selecting every $c^{th}$ bit from the signature, where c is the compression factor.

28. The method of claim 26, wherein the determining the thumbnail signature comprises selecting every $c^{th}$ data point, where c is the compression factor.

29. The method of claim 26, wherein the determining the thumbnail signature comprises averaging adjacent groups of data points.

30. The method of claim 25, wherein the determining the thumbnail signature comprises averaging adjacent groups of bits of the signature.

* * * * *